(12) United States Patent
Gould et al.

(10) Patent No.: US 7,352,459 B2
(45) Date of Patent: Apr. 1, 2008

(54) SCANNING SPECTROPHOTOMETER FOR HIGH THROUGHPUT FLUORESCENCE DETECTION AND FLUORESCENCE POLARIZATION

(75) Inventors: Gene Gould, Cardiff, CA (US); Michael J. Conrad, Escondido, CA (US)

(73) Assignee: Chromagen, Inc., Escondido, CA (US)

( * ) Notice: Subject to any disclaimer, the term of this patent is extended or adjusted under 35 U.S.C. 154(b) by 43 days.

(21) Appl. No.: 10/039,769

(22) Filed: Dec. 31, 2001

(65) Prior Publication Data

US 2002/0109841 A1 Aug. 15, 2002

(Under 37 CFR 1.47)

Related U.S. Application Data

(60) Provisional application No. 60/259,326, filed on Dec. 29, 2000.

(51) Int. Cl.
*G01J 3/18* (2006.01)
*G01N 21/64* (2006.01)

(52) U.S. Cl. ............ 356/318; 356/333; 250/458.1
(58) Field of Classification Search ............ 356/300, 356/305, 318, 319, 322, 326, 327, 328; 250/458.1, 250/461.1
See application file for complete search history.

(56) References Cited

U.S. PATENT DOCUMENTS

| | | | | |
|---|---|---|---|---|
| 3,715,585 A | * | 2/1973 | Harrick | |
| 3,825,762 A | | 7/1974 | White | ............... 250/458 |
| 3,886,363 A | * | 5/1975 | Ohnishi et al. | |
| 4,352,561 A | * | 10/1982 | Tohyama et al. | |
| 4,355,871 A | * | 10/1982 | Nevyas et al. | ............... 351/212 |
| 4,546,256 A | * | 10/1985 | Denisov et al. | ............... 250/372 |
| 4,678,326 A | | 7/1987 | Harjunmaa | ............... 356/73 |
| RE32,598 E | * | 2/1988 | White | ............... 356/318 |
| 4,973,159 A | * | 11/1990 | Sohma et al. | |
| 5,018,866 A | | 5/1991 | Osten | ............... 356/417 |
| 5,233,405 A | * | 8/1993 | Wildnauer et al. | ............... 356/333 |
| 5,662,400 A | * | 9/1997 | Shikama et al. | |
| 5,946,090 A | * | 8/1999 | Tashiro et al. | |
| 6,040,904 A | * | 3/2000 | Fallet et al. | ............... 356/236 |
| 6,654,119 B1 | * | 11/2003 | Gould et al. | ............... 356/318 |

FOREIGN PATENT DOCUMENTS

| | | |
|---|---|---|
| DE | 26 28 551 A | 12/1977 |
| GB | 2 119 507 A | 11/1983 |
| JP | 63-289427 | 11/1988 |
| WO | WO 00 63680 | 10/2000 |

* cited by examiner

*Primary Examiner*—Hwa (Andrew) Lee
(74) *Attorney, Agent, or Firm*—Pillsbury Winthrop Shaw Pittman LLP

(57) ABSTRACT

A fluorescence spectrophotometer system may be implemented in scanning fluorescence polarization detection applications. A wavelength and area scanning fluorescence spectrophotometer system may include a light source, an excitation double monochromator, an excitation/emission light transfer module, an emission double monochromator, a high speed timer-counter circuit board, a precision positioning apparatus for positioning a sample relative to the focal plane of the excitation light, and polarizing filters at the excitation side and the emission side. The system may be operative to analyze more than one fluorescent compound in the sample; additionally or alternatively, the system enables analysis of samples from selected ones of a plurality of samples.

65 Claims, 13 Drawing Sheets

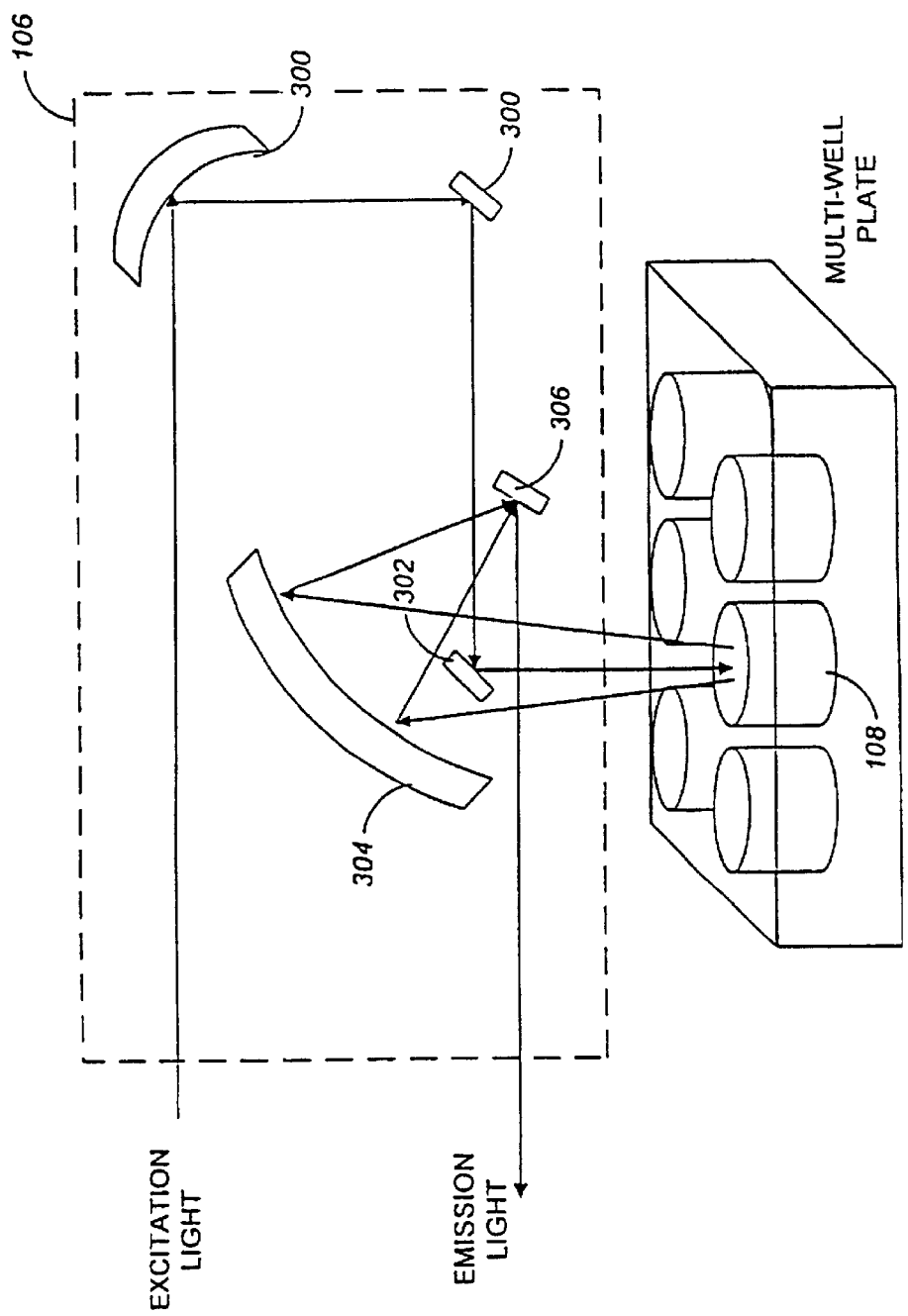

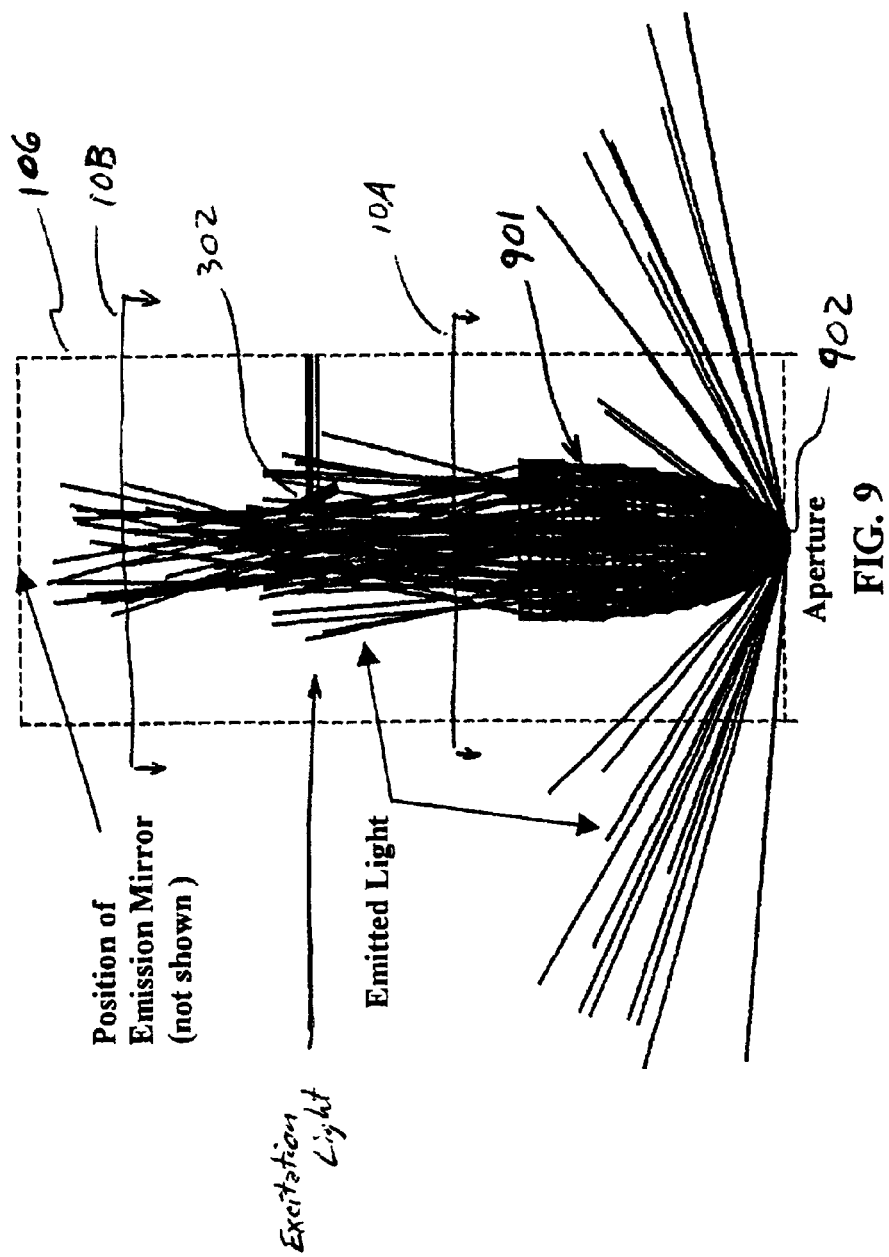

SCANNING SPECTROPHOTOMETER FOR HIGH THROUGHPUT FLUORESCENCE DETECTION AND FLUORESCENCE POLARIZATION

The present application claims the benefit of a provisional application, Ser. No. 60/259,326, filed Dec. 29, 2000, entitled "SCANNING SPECTROPHOTOMETER FOR HIGH THROUGHPUT FLUORESCENCE DETECTION AND FLUORESCENCE POLARIZATION."

TECHNICAL FIELD

Aspects of the present invention relate generally to wavelength scanning fluorescence spectrophotometers using dual grating monochromators, but not optical filters, to select excitation and emission wavelengths of light and to detect and to quantify simultaneous fluorescence emission, including polarized fluorescence emission, from multiple fluorophores in the same sample.

BACKGROUND

Definitions:

1) FLUORESCENCE: The result of multi-stage process of energy absorption and release by electrons of certain naturally occurring minerals, polyaromatic hydrocarbons and other heterocycles.

2) EXCITATION: Photons of energy, $e=h\nu_{exc}$, are supplied by a light source and absorbed by an outer electron of a fluorophore, which is elevated from the ground state, $S_0$, to an excited electronic singlet state, $S'_1$.

3) EXCITED STATE LIFETIME: An excited electron remains in the singlet state for a finite period, typically from 1 to 20 nanoseconds, during which the fluorophore undergoes a variety of changes including conformational changes and alterations in the interaction with solvent. As a result of these changes, the energy of the $S_1$, singlet electron partially dissipates to a relaxed singlet excited state, $S_1$.from which fluorescence emission of energy occurs, returning the electron to the ground state, $S_0$.

4) EMISSION: Photons of energy, $e=h\nu_{em}$, are released from an excited state electron, which returns the fluorophore to the ground state. Owing to energy loss during the excited state lifetime, the energy of these photons is lower than that of the exciting photons, and the emitted light is of longer wavelength. The difference in the energy (or wavelengths) is called the Stoke's shift and is an important feature in the selection of a dye for use as a label or in a probe. The greater the Stoke's shift, the more readily low numbers of photons can be distinguished from background excitation light.

5) FLUOROPHORES: Fluorescent molecules are generally referred to as fluorophores. When a fluorophore is utilized to add color to some other molecule, the fluorophore is called a fluorescent dye and the combination is referred to as a fluorescent probe. Fluorescent probes are designed to: 1) localize and help visualize targets within a specific region of a biological specimen, or, 2) respond to a specific stimulus.

6) ELECTROMAGNETIC SPECTRUM: The entire spectrum, considered as a continuum, of all kinds of electric and magnetic radiation, from gamma rays, having a wavelength of 0.001 Angstroms to long waves having a wavelength of more than 1,000,000 kilometers and including the ultraviolet, visible and infrared spectra.

7) FLUORESCENCE SPECTRUM: Unless a fluorophore is unstable (photobleaches), excitation and emission is a repetitive process during the time that the sample is illuminated. For polyatomic molecules in solution, discrete electronic transitions are replaced by broad energy bands called the fluorescence excitation and fluorescence emission spectra, respectively.

8) MONOCHROMATOR: A device which admits a wide spectral range of wavelengths from the electromagnetic spectrum via an entrance aperture, and, by dispersing wavelengths in space, makes available at an exit aperture only a narrow spectral band of prescribed wavelength(s). Optical filters differ from monochromators in that they provide wavelength selection through transmittance of selected wavelengths rather than through spatial dispersion. A second distinguishing feature of a monochromator is that the output wavelength(s), and in many cases, the output spectral bandwidth, may be continuously selectable. Typically, the minimal optical components of a monochromator comprise:

(a) an entrance slit that provides a narrow optical image;
(b) a collimator which ensures that the rays admitted by the slit are parallel;
(c) some component for dispersing the admitted light into spatially separate wavelengths;
(d) a focusing element to re-establish an image of the slit from selected wavelengths; and,
(e) an exit slit to isolate the desired wavelengths of light.

In a monochromator, wavelength selection is achieved through a drive system that systematically pivots the dispersing element about an axis through its center. Slits are narrow apertures in a monochromator which may have adjustable dimensions. Slits effect selection of the desired wavelength(s) and their dimensions may be adjustable.

9) DUAL GRATING MONOCHROMATOR: A monochromator containing two gratings coupled in series. The second grating accepts wavelengths of light selected by the first and further separates the prescribed ed wavelengths from undesired wavelengths.

10) WAVELENGTH SCANNING: Continuous change of the prescribed output wavelength(s) leaving the exit slit of a monochromator. In a spectrophotometer, wavelengths of the electromagnetic spectrum are scanned by the excitation monochromator to identify or prescribe the wavelength(s) at which a fluorophore is excited, wavelength scanning by the emission monochromator is used to identify and detect the wavelength(s) at which a fluorophore emits fluorescent light. In automated fluorescence spectrophotometers, wavelength scanning by the excitation and emission monochromators may be performed either separately or concurrently (synchronous scanning).

11) AREA SCANNING: Area scanning is distinct from wavelength scanning and is the collective measurement of local fluorescence intensities in a defined two dimensional space. The result is an image, database or table of intensities that maps fluorescence intensities at actual locations in a two dimensional sample. At its simplest, area scanning may be a photograph made with a camera in which all data are collected concurrently. Alternatively, the sample may be moved past a detector which measures the fluorescence in defined sub-areas of a sample. The collected information creates a matrix which relates fluorescence intensity with position from which an image, table or graphical representation of the fluorescence in the original sample can be created.

12) FLUORESCENCE DETECTORS

Five elements of fluorescence detection have been established through laboratory use of fluorophores during the last two decades:

(a) an excitation source,
(b) a fluorophore, (c) some type of wavelength discrimination to isolate emission photons from excitation photons, (d) some type of photosensitive response element that converts emission photons into a recordable form, typically an electronic signal or a photographic image, and, (e) a light tight enclosure to restrict ambient light.

Fluorescence detectors are primarily of four types, each providing distinctly different information:

(a) Cameras resolve fluorescence as spatial coordinates in two dimensions by capturing an image: [a] as a photographic image on highly sensitive film, or, [b] as a reconstructed image captured on arrays of pixels in a charge coupled device (CCD).

(b) Fluorescence microscopes also resolve fluorescence as spatial coordinates in two or three dimensions. Microscopes collect all of the information for an image for a prescribed visual field at the same time without any movement of either the sample or the viewing objective. A microscope may introduce qualitative estimation of fluorophore concentration through use of a camera to capture an image in which case the measure is a function of exposure time.

(c) Flow cytometers measure fluorescence per biological cell in a flowing liquid, allowing subpopulations within a mixture of cells to be identified, quantitated, and in some cases separated. Flow cytometers cannot be used to create an image of a defined area or perform wavelength scanning. The excitation light source is invariably a laser and wavelength discrimination is accomplished through some combination of tunable dye lasers and filters. Although these instruments may employ photomultiplier tubes (PMTs) to detect a measurable signal, there are no flow cytometers that employ monochromators for wavelength scanning.

(d) Spectrofluorometers (spectrophotometer(s)) typically employ a PMT to detect fluorescence but can measure either: [a] the average current evoked by fluorescence over time (signal averaging), or, [b] the number of photons per unit time emitted by a sample (photon counting).

Fluorescence spectrophotometers are analytical instruments in which a fluorescent dye or probe can be excited by light at specific wavelengths, and, concurrently, have its emitted light detected and analyzed to identify, measure and quantitate the concentration of the probe. For example, a piece of DNA may be chemically attached, or labeled, with fluorescent dye molecules that, when exposed to light of prescribed wavelengths, absorb energy through electron transitions from a ground state to an excited state. As indicated above, the excited molecules release excess energy via various pathways, including fluorescence emission. The emitted light may be gathered and analyzed. Alternatively, a molecule of interest may be conjugated to an enzyme which can convert a specific substrate molecule from a non-fluorescent to a fluorescent product following which the product can be excited and detected as described above.

The ranges of excitation and emission wavelengths employed in a fluorescence spectrophotometer typically are limited to the ultraviolet and visible portions of the electromagnetic spectrum For the purposes of fluorescence detection, useful dyes are those which are excited by, and emit fluorescence at, a few, narrow bands of wavelengths within the near ultraviolet and visible portions of the electromagnetic spectrum Desired wavelengths for excitation of a specific fluorescent molecule may be generated from 1) a wide band light source by passing the light through a series of bandpass filters (materials which transmit desired wavelengths of light and are opaque to others), or cut-on filters (materials which transmit all wavelengths longer or shorter than a prescribed value),
2) a narrow band light source such as a laser, or,
3) an appropriate monochromator.

For a wide band light source, the light to which a fluorescent dye is exposed is typically isolated through bandpass filters to select a desired wavelength from the ultraviolet or visible spectrum for use in excitation. In monochromator-based instruments, the wavelength of choice is obtained after light from the source has been dispersed into a spectrum from which the desired wavelength is selected. Whatever the light source, the fluorescence emission is typically isolated through bandpass filters, cut-on filters, or emission monochromators to select a desired wavelength for detection by removal of all light of any wavelengths except the prescribed wavelengths. Most fluorescence detection involves examination of specimens that are in a liquid phase. The liquid can be contained in a glass, plastic or quartz container which can take the form of, for example: an individual cuvette; a flow-through cell or tube; a microscope slide; a cylindrical or rectangular well in a multiwell plate; or silicon microarrays which may, have many nucleic acids or proteins attached to their surfaces. Alternatively, the liquid can be trapped in a two-dimensional polyacrylamide or agarose gel. In each of these cases, light which has already passed through the optical filters to select the correct wavelengths for excitation illuminates the sample in the container or gel; concurrently, emitted light is also collected, passed through a second set of optical filters to isolate the wavelengths of emission, and then detected using a camera, or photosensor.

The optical filters used in fluorescence detectors present characteristics that limit the sensitivity, dynamic range and flexibility of fluorescence detection, including: light absorption which causes a loss of efficiency through the system inherent auto-fluorescence, which produces a high background signal; transmission of other wavelengths outside the wavelengths of desired bandpass which, in turn limits both sensitivity and dynamic range. Optical filters must be designed and manufactured to select for discrete ranges of wavelengths ("center-width bandpasses") which limits fluorescence detection to the use of compounds which are excited and emit at wavelengths appropriate for those filters. Development of a new fluorescent dye with unusual spectral properties may necessitate design of a new excitation/emission filter pair.

To increase efficiency in fluorescence cuvette spectrophotometers as well as to provide continuous selection of wavelengths, it has been known to use grating or prism-based monochromators to disperse incoming light from an excitation source, select a narrow band of excitation wavelengths and, separately, to select an emission wavelength. Gratings come in many forms but are etched with lines that disperse broadband light into its many wavelengths. A monochromator typically includes a light-tight housing with an entrance slit and an exit slit. Light from a source is focused onto the entrance slit. A collimating mirror within the housing directs the received beam onto a flat optical grating, which disperses the wavelengths of the light onto a second collimating mirror which in turn focuses the now linearly dispersed light onto the exit slit. Light of the desired wavelength is selected by pivoting the grating to move the linear array of wavelengths past the exit slit, allowing only a relatively narrow band of wavelengths to emerge from the monochromator. The actual range of wavelengths in the selected light is determined by the dimensions of the slit. The process of continuous selection of a narrow band of wavelengths from all wavelengths of a continuous spectrum is referred to as wavelength scanning and the angle of rotation of the dispersing optical grating with respect to the entrance and exit slits correlates with the output wavelength of the monochromator. In order to select the wavelengths of excitation and fluorescence detection, it has been known to use two gratings in each monochromator to enhance wavelength selection for both the excitation and emission light in a fluorescence spectrophotometer. While the monochromators potentially eliminate the need to use optical filters for wavelength selection and free the scientist from the limitations of filters, their use imposes other limitations on instrument sensitivity and design. For example, monochromators having the configurations described above have the disadvantage of requiring at least four mirrors and two dispersing elements, along with associated light blocking entrance and exit slits. Consequently, such devices have been relatively complex and comparatively inefficient compared to filter based instruments.

Analysis of multiple samples in multi-well plates is a highly specialized use of fluorescence spectrophotometers. Typically, the excitation light is introduced into a well from a slight angle above the well in order to allow the majority of the fluorescence emission light from the sample within a well to be collected by a lens or mirror. However, as the number of wells per plate is increased (e.g., from 96 wells per plate to in excess of 9600 per plate), this side illumination configuration becomes disadvantageous, since most of the incoming excitation light strikes the side of the well rather than the sample. Since such wells typically have black side walls, much of the excitation light is lost.

As mentioned above, one method employed to overcome the limitations of side illumination configurations has been use of an optical fiber to guide the excitation light to an illumination end of the fiber directly positioned over a well. A second bundle of fibers is employed to collect light from the well and transmit it to the PMT. In a variation of this design, a bifurcated optical fiber positioned above a microwell has been used to carry light both into and out of the well However, optical fibers typically introduce absorption losses and may also auto-fluoresce at certain wavelengths. Accordingly, such a solution is not particularly efficient.

Another approach has been to use multi-well plates with transparent bottoms, and exposing a sample within a well to excitation light from the bottom while collecting emission light from the open top. While this approach has value in some circumstances, light is lost from absorption as well as from light scattering by the plastic at the well bottom, Additionally, the transparent plate material may itself auto-fluoresce. In addition, well-to-well optical reproducibility of the well bottom material has not been achieved, which has limited the ability to correlate measurements on a well-to-well or plate-to-plate basis. Accordingly, such a solution has proven to be less efficient than illuminating and collecting light from the same side of a sample.

Examples of such prior art using fiber optic light paths include a single unit fluorescence microtiter plate detector (the "Spectromax GEMINI") introduced in 1998 by Molecular Devices, which employs a hybrid combination of single grating monochromators, filters, mirrors and optical fibers, and the "Fluorolog-3", a modular instrument, and the "Skin-Sensor", a unitized instrument, both produced by Instruments SA, both of which employ bifurcated fiber optic bundles to conduct light from an excitation monochromator and to collect light from a sample after which it is transmitted to the excitation monochromator.

It should be noted that microtiter plate applications of fluorescence monochromators are also limited to microwell plates with 384, 96, or fewer wells; that is, 1536-well microplates, as well as "nanoplates" containing 2500 wells, 3500 wells, and even 9600 wells cannot be used with the current fiber-optic/monochromator based instruments. Detectors for such plates typically use lasers and filters combined with confocal microscopy.

For the large number of applications involving glass microscope slides, polyacrylamide gels or standard 96-well, 384-well and 1536-well microwell plates, it would be desirable to have a fluorescence spectrophotometer that provides high efficiency, enables high precision continuous excitation and emission wavelength selection, provides significantly greater dynamic range, eliminates the use of optical filters and optical fibers (i.e., light paths do not pass through any optical materials other than air), and has a highly efficient structure for both guiding the excitation light onto a sample and collecting the emission light from the sample in a microtiter well or on a two dimensional surface such as a glass microscope slide, polyacrylamide gel, silicon microarray, or other solid surfaces.

In general, the measurement of fluorescent light intensity, the luminescence, is defined as the number of photons emitted per unit time. Fluorescence emission from atoms or molecules can be used to quantitate the amount of an emitting substance in a sample. The relationship between fluorescence intensity and analyte concentration is:

$$F = k\, Q_e P_o\, (1 - 10^{[\in bc]})$$

where F is the measured fluorescence intensity, k is a geometric instrumental factor, $Q_e$ is the quantum efficiency (photons emitted/photons absorbed), $P_o$ is the probability of excitation which is a function of the radiant power of the excitation source, $\in$ is the wavelength dependent molar absorptivity coefficient, b is the path length, and c is the analyte concentration. In previous applications, the above equation was simplified by expanding the equation in a series and dropping the higher terms to give:

$$F = k\, Q_e P_o\, (2.303 * \in * b * c).$$

In the past, this relationship was acceptable because fluorescence intensity appeared to be linearly proportional to analyte concentration. The equation fails, however, to provide for true comparison of the fluorescence intensities of different fluorophores because measurement of fluorescence intensity is highly dependent upon k, the geometric instrumental factor.

Different types of detectors vary in both the time period during which a measurement is made and the speed at which each can discriminate between photons, characteristics which can be of critical importance when comparing the luminosity of two fluorophores. Consider two fluorescent dyes that differ only in that the excited state lifetime of one is tenfold longer than that of the excited state lifetime of the second fluorophore (e.g. 1 nanosecond and 10 nanoseconds, respectively). When detected using photographic film exposed for a defined exposure time, the dye with the shorter lifetime would clearly appear brighter on the exposed film. However, if a detector employing continuous excitation were used which could not discriminate between photons at a high enough frequency, the fluorophore with the shorter excited state lifetime could actually be emitting far more photons but the detector could erroneously indicate that the fluorescence intensity of the two dyes was the same.

Fluorescence is detected in spectrophotometers through generation of photocurrent in an appropriate photosensitive device such as a PMT or other photosensing device, both of which are characterized by low levels of background or random electronic noise. For this reason, fluorescent emission processes are best characterized by Poisson statistics and fluorescence can be measured through either photon counting or signal averaging:

Photon counting is a highly sensitive technique for measurement of low levels of electromagnetic radiation. In photon counting detection, current produced by a photon hitting the anode of a PMT with sufficient energy to begin an avalanche of electrons is tested by a discriminator circuit to distinguish between random electronic noise and true signal. At such light levels, the discreteness of photons dominates measurement and requires technologies that enable distinguishing electrical pulses that are photon-induced from dark-current impulses that originate in the detector (e.g. a PMT) from other causes.

In previous applications of photon counting, the dynamic range of detection was restricted by the ability of the detector to discriminate between photons closely spaced in time. Additionally, the signal to noise ratio in photon counting is also a function of the light intensity. Assume a steady light flux incident on a photocathode producing m photo-electrons per second. During any one second, the light incident on the photocathode is, on average, m photoelectrons with a standard deviation of $m^{1/2}$. The signal to noise ratio in such measurements is:

$$S/N = m/m^{1/2} = m^{1/2} \quad (1)$$

Depending upon their frequency and energy, individual photoelectrons can be counted with a detector of sufficient gain, but the precision of any measurement can never be better than the limit imposed by equation (1). In its simplest form, a practical photon counting instrument consists of a fast amplifier and a discriminator set to a low threshold relative to the input, typically −2 mV, which has been found empirically to correspond to the optimum compromise between susceptibility to electrical pickup and operating the photomultiplier at excessive gain.

Theoretically less sensitive than photon counting and with greater sensitivity to electronic drift, signal averaging uses photocurrent as a direct measure of the incident light signal. The noise associated with the photocurrent $I_k$, taking the system bandwidth (frequency of response), B, into account, is given by the shot noise formula:

$$S/N = (I_k/2eI_kB)^{1/2} \quad (2)$$

where e is the electronic charge. The forms of equations 1 and 2 are similar, since they refer to the same phenomenon and predict essentially the same result. In contrast to photon counting in which the signal is inherently digitized and its dynamic range limited by the speed of the timer counter, in equation 2 the signal is taken as a continuous variable of the photocurrent and it is possible to obtain a much larger dynamic range. In practice, however, the analog-to-digital conversion process severely limits the dynamic range owing to the slow response times associated with A/D converters having more than 16-bit resolution.

In general purpose fluorescence detection instruments, the light source can be a quartz halogen lamp, a xenon lamp or similar gas discharge lamp, a photodiode or one of many types of lasers. Typically the sample is exposed to continuous illumination which maintains a relatively stable percentage of the total number of fluorophores in an excited state. In these instruments, the cross-sectional dimension of the sample which is illuminated is principally determined by slits. In more complex instruments, including any using imaged light, confocal optics or point source illumination, the exciting light beam is shaped and focused by lenses and mirrors onto a single point and a single focal plane in the sample.

SUMMARY

According to various embodiments of the present invention, a wavelength and area scanning fluorescence spectrophotometer is provided that includes an excitation double monochromator, a coaxial excitation/emission light transfer module, an emission double monochromator, a high speed timer-counter circuit board, and a precision x-y-z mounting table for use in positioning a sample relative to the focal plane of the excitation light. Operations of each are directed and coordinated through a timer-counter board.

Each monochromator may include a pair of holographic concave gratings mounted to select a desired band of wavelengths precisely from incoming broadband light. Selected excitation light is directed into a sample well or onto a two dimensional surface such as a polyacrylamide gel or microscope slide by a light transfer module that includes a coaxial excitation mirror positioned to direct excitation light directly into a well of a multi-well plate or onto a particular area of a gel, microscope slide, or microarray. Emitted light that exits the illuminated area or the sample is collected by a relatively large front-surfaced mirror. The collected emission light is wavelength selected by the emission double monochromator. Both monochromators contain three precision matched apertures that are positioned to restrict unwanted wavelengths while simultaneously creating a "near point" source of the desired wavelengths for the succeeding stage of the optical path. Emission light that has been isolated in this way is projected onto the photodetector and analyzer module which converts the received energy into a digital representation of the fluorescence intensity of the sample.

One embodiment includes a fluorescence spectrophotometer system having a light source; a first double monochromator operating to separate and output selected wavelengths of light from the light source as excitation light; a light transfer module for directing substantially all of the excitation light directly onto a sample and for collecting, focusing, and directing fluorescent or luminescent light from the sample as emission light; a second double monochromator operating to separate and output selected wavelengths of the emission light; and a photodetector and analyzer for detecting the selected wavelengths of emission light and outputting an indication of such detection.

Another embodiment includes a double monochromator having an entrance aperture for accepting light; a first optical grating positioned to intercept and to disperse at least part of the light accepted through the entrance aperture; a first selection aperture positioned to intercept part of the light dispersed by the first optical grating and to select and pass a narrowed range of wavelengths from such dispersed light; a second optical grating positioned to intercept and disperse at least part of the light passed through the first selection aperture; and a second selection aperture positioned to intercept part of the light dispersed by the second optical grating and to select and pass a narrowed range of wavelengths from such dispersed light.

Yet another embodiment includes a light transfer module having an excitation mirror, positioned substantially coaxial with an area to be illuminated, for directing incoming light to illuminate the area; and an emission mirror, positioned substantially coaxial with the area that has been illuminated and in off-axis alignment with the excitation mirror, for collecting, focusing, and directing light emitted by the area upon illumination.

Another embodiment includes a photon counting photodetector and high speed timer-counter board which largely eliminates instrument drift, provides great sensitivity while enabling high frequency discrimination of photons for maximum resolution and quantitation and, concurrently, provides significantly greater dynamic range.

In accordance with another embodiment, a fluorescence spectrophotometer system additionally includes an optical polarizing filter operative to restrict the excitation light to plane polarized excitation light and an optical filter holder selectively operative to insert the optical polarizing filter into the path of the excitation light. The optical filter and the optical filter holder may be incorporated into the first double monochromator described above; alternatively, the optical filter and the optical filter holder may be incorporated into the light transfer module.

Additionally, the foregoing system may also include a first polarizing filter operative to transmit emission light in a plane which is parallel to the plane of the polarized excitation light, a second polarizing filter operative to transmit emission light in any plane which is not parallel to the plane of the polarized excitation light, and a polarizing filter holder selectively operative to insert one of the first polarizing filter or the second polarizing filter into the path of the emission light. As with the optical filter, the first polarizing filter, the second polarizing filter, and the polarizing filter holder may alternatively be incorporated into the second double monochromator or the light transfer module. When incorporated into the light transfer module, such emission polarizer filters may be interposed between the illuminated area and the emission mirror; i.e. upstream of the emission mirror.

In other embodiments set forth in more detail below, a fluorescence spectrophotometer system may incorporate a light source comprising a spherical concave reflector system having interchangeable apertures, the reflector system being telecentric at both ends and fully corrected for third order aberrations, a first multiple-grating monochromator having an entrance aperture, the first multiple-grating monochromator being operative to separate light imaged onto the entrance aperture from the light source into a plurality of wavelengths and to output selected wavelengths as excitation light, and a light transfer module comprising a first reflection surface operative to direct substantially all of the excitation light directly onto a sample and a second reflection surface, the second reflection surface being a compound parabolic reflective surface and operative to collect, focus, and direct light emitted from the sample as fluorescent or luminescent light.

In still other embodiments, elements of the system including the light transfer module, the second multiple-grating monochromator, and the photodetector and analyzer are operative to analyze more than one fluorescent compound in the sample. Additionally or alternatively, a spectrophotometer system may comprise means for translating a sample or sample holder, such as a microwell plate, for example, relative to the light transfer module allowing analysis of samples from selected ones of a plurality of wells in the microwell plate.

In accordance with another aspect as set forth in detail below, a method of analyzing a sample generally comprises providing excitation light from a light source, directing the excitation light through a first double monochromator, transmitting the excitation light to the sample through a light transfer module, employing the light transfer module to obtain light emitted by the sample, directing the light emitted by the sample to a second double monochromator, and analyzing light output by the second double monochromator. The method may be employed to detect and to analyze more than one fluorescent compound in a single sample.

The foregoing and other aspects of various embodiments of the present invention will be apparent through examination of the following detailed description thereof in conjunction with the accompanying drawings.

DESCRIPTION OF DRAWINGS

FIG. 3 is a simplified schematic diagram of one embodiment of the light transfer module shown in FIG. 1.

FIG. 9 is a simplified cross-sectional diagram of one embodiment of a light transfer module incorporating a compound parabolic concentrator.

Unless otherwise noted, like reference numerals and designations in the various drawings indicate like components.

DETAILED DESCRIPTION

Figure 1:
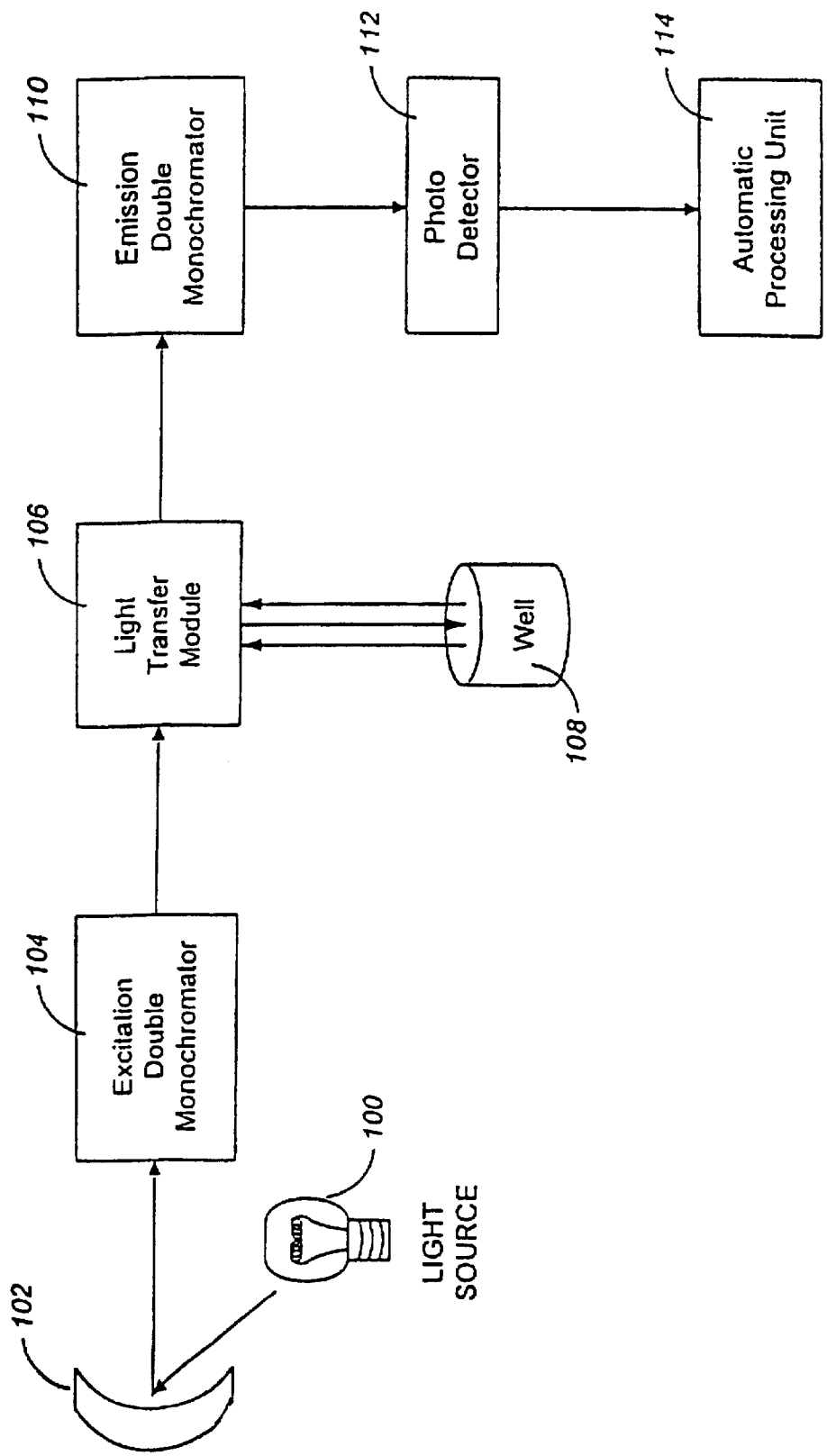
FIG. 1 is a schematic diagram of an embodiment of a fluorescence spectrophotometer system

FIG. 1 is a schematic diagram of one exemplary embodiment of a fluorescence spectrophotometer system constructed and operative in accordance with the present invention. A broadband light source 100 illuminates a mirror 102, which is suitably curved to focus the light onto a double monochromator 104. In alternative configurations, a narrow band light source such as a photodiode or a laser may be substituted for the broadband light source depicted in FIG.

1; those of skill in the art will appreciate that such a narrow band light source may be implemented in conjunction with the any or all of the fluorescence spectrophotometer systems and monochromator configurations set forth in detail below.

In some alternative embodiments, for example, light source 100 may comprise a halogen cycle tungsten filament lamp or other suitable lamp operative to transmit light to a spherical concave reflector system having interchangeable apertures; as described below, such a reflector system may be telecentric at both ends of the optical train and fully corrected for third order aberrations.

Light of the desired wavelength is passed by an excitation double monochromator 104 to a light transfer module (LTM) 106. The LTM 106 directs the excitation light from monochromator 104 onto a sample 108, which can be, for example, one well of a microwell plate or one lane of a 1-D polyacrylamide gel. Any resulting fluorescent or luminescent light emitted by the sample may be collected by LTM 106 as set forth below; LTM 106 may direct the light to the entrance aperture of an emission double monochromator 110. In operation, monochromator 110 may be selectively adjusted to pass wavelengths from the emission spectrum of the fluorophore(s) in the sample, and is operative to direct those wavelengths to a photodetector 112, which measures the energy of the emitted light.

Photodetector 112 may be any suitable photosensitive device, including but not limited to a photomultiplier tube (PMT), a phototransistor, or a photodiode. The electronic output of photodetector 112 may be applied to an automatic processing unit 114, which generates a signal (which may be stored in a numerical form suitable for further analysis) indicating detection of the selected emission. Automatic processing unit 114 may be, for example, a personal computer having a data collection interface to the spectrophotometer system In general, all of the elements of the optical pathways in the instrument depicted in FIG. 1, including double monochromators 104 and 110 and the LTM 106, may be isolated in light-tight boxes coated internally with non-fluorescent absorptive material to minimize reflectance and light from other sources such as room light.

Figure 2A:
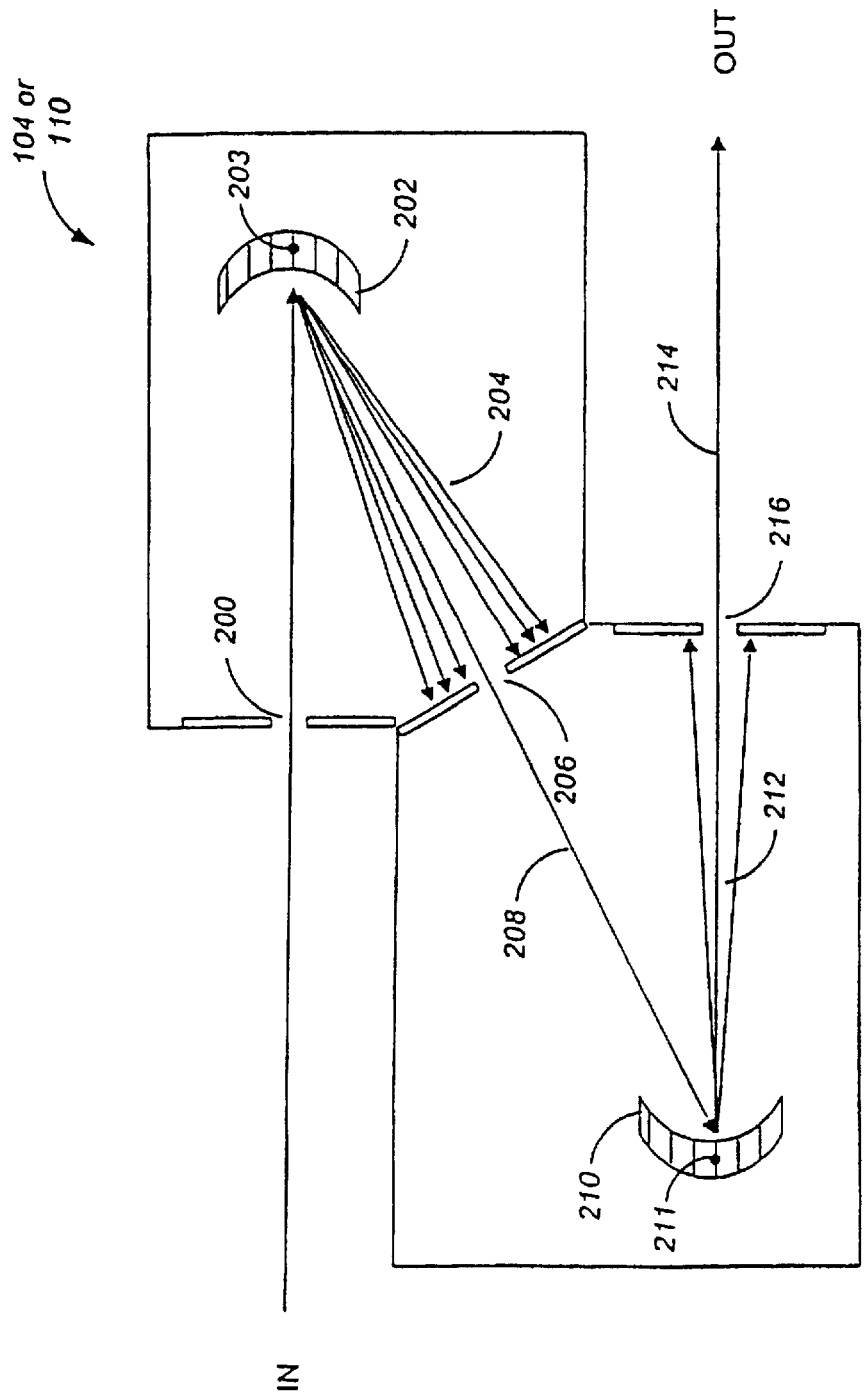
FIG. 2A is a schematic diagram of an embodiment of a double monochromator.

FIG. 2A is a schematic diagram of an embodiment of a double monochromator configured and operative for use in embodiments of a fluorescence spectrophotometer system The illustrated configuration may be used for either the excitation double monochromator 104 or the emission double monochromator 110 illustrated in FIG. 1.

Broadband light is introduced through an entrance aperture 200 in the double monochromator and reflects off the front surface of a first holographic concave grating 202 that is pivotable about an axis 203. Use of front surface reflection enhances the efficiency of a double monochromator by avoiding absorption of light within an optical support structure, such as in a rear surface reflection glass mirror. Use of a concave grating allows incident light to be dispersed into selectable wavelengths without the use of supplemental collimating mirrors. This design makes it possible to eliminate two collimating mirrors per grating used in conventional dual monochromator instruments. Use of a holographic grating also reduces astigmatic aberrations, and thus decreases the amount of light of unwanted wavelengths ("stray light").

Each double monochromator has three apertures: an entrance aperture 200, through which light first enters the monochromator; an internal (or "first") selection aperture 206; and an exit (or "second") selection aperture 216, through which light exits the monochromator. The first concave grating 202 reflects wavelengths of the incoming light as a first spatially dispersed beam 204. Each wavelength of this first spatially dispersed beam 204 is reflected at a unique angle relative to other wavelengths. Pivoting first concave grating 202 about its axis 203 enables a selected band or range of wavelengths 208 to be directed through the internal selection aperture 206 within the monochromator housing.

The selected range of wavelengths 208 is then reflected off a second holographic concave grating 210 that is pivotable about an axis 211. Second concave grating 210 reflects the selected range of wavelengths 208 of the first spatially dispersed beam 204 as a second spatially dispersed beam 212. Pivoting second concave grating 210 about its axis 211 enables a selected narrow band of wavelengths 214 to be directed through exit selection aperture 216.

The dimensions of selection apertures 206 and 216 determine the selected wavelengths of light leaving the monochromator. Wider apertures allow more light energy to pass through a monochromator, but the light includes a broad range of wavelengths; narrower apertures reduce the amount of light passing through a monochromator but narrow the selected range of wavelengths. The use of wider apertures increases the sensitivity of detection, which may be beneficial in measurements of total fluorescence in an area or volume (e.g. measurements made in microwells). In contrast, the use of narrow apertures increases the spatial resolution of a monochromator, which may be beneficial in discriminating between different fluorophores at particular locations (e.g. measurements of bands separated in a polyacrylamide gel). That is, the smaller the aperture dimensions, the smaller the area of detection at the sample. In the case of laser light sources and pinhole apertures, for example, the area of excitation at any given moment is a point that corresponds to a particular data pair representing fluorescent intensity and position.

It is generally known by those of skill in the art of optical systems that each optical component reduces the efficiency of light throughput. Advantages of the configuration shown in FIG. 2A include, but are not limited to, elimination of collimating mirrors for redirecting light within the double monochromator, such as is the case with traditional monochromators. In the exemplary embodiment, only two light directing elements (the first and second holographic concave gratings 202, 210) are required, thus improving overall light efficiency.

In the configuration illustrated in FIG. 2A, the first concave grating 202 and the second concave grating 210 may be pivoted oppositely and in tandem by a suitable mechanism. A mechanism according to one embodiment (illustrated in FIG. 2B) implements a tension band actuator mechanism for pivoting gratings 202, 210. In the FIG. 2B configuration, gratings 202, 210 are mounted coaxially with pivot wheels 250, 252, respectively. One end of a lever arm 254 is connected to pivot wheel 250; the other end of lever arm 254 is coupled to a screw drive mechanism 256. Lever arm 254 traverses along threaded rod 258 as the rod 258 is rotated by a motor 260.

Lever arm 254 movement along rod 258 causes pivot wheel 250 to rotate. Pivot wheel 250 is connected to pivot wheel 252 by a tension band 262. In accordance with the FIG. 2B embodiment, tension band 262 may be a 0.003 inch stainless steel band. Tension band 262 causes pivot wheel 252 and grating 210 to counter-rotate synchronously and in tandem with pivot wheel 250 and grating 202. A spring 264 connected between a housing (not shown) and pivot wheel 252 maintains tension in tension band 262. The position (i.e. angular orientation) of gratings 202,210 may be determined and controlled by a microcontroller connected to pivot wheel sensor 266 and screw drive sensor 268.

Figure 2B:
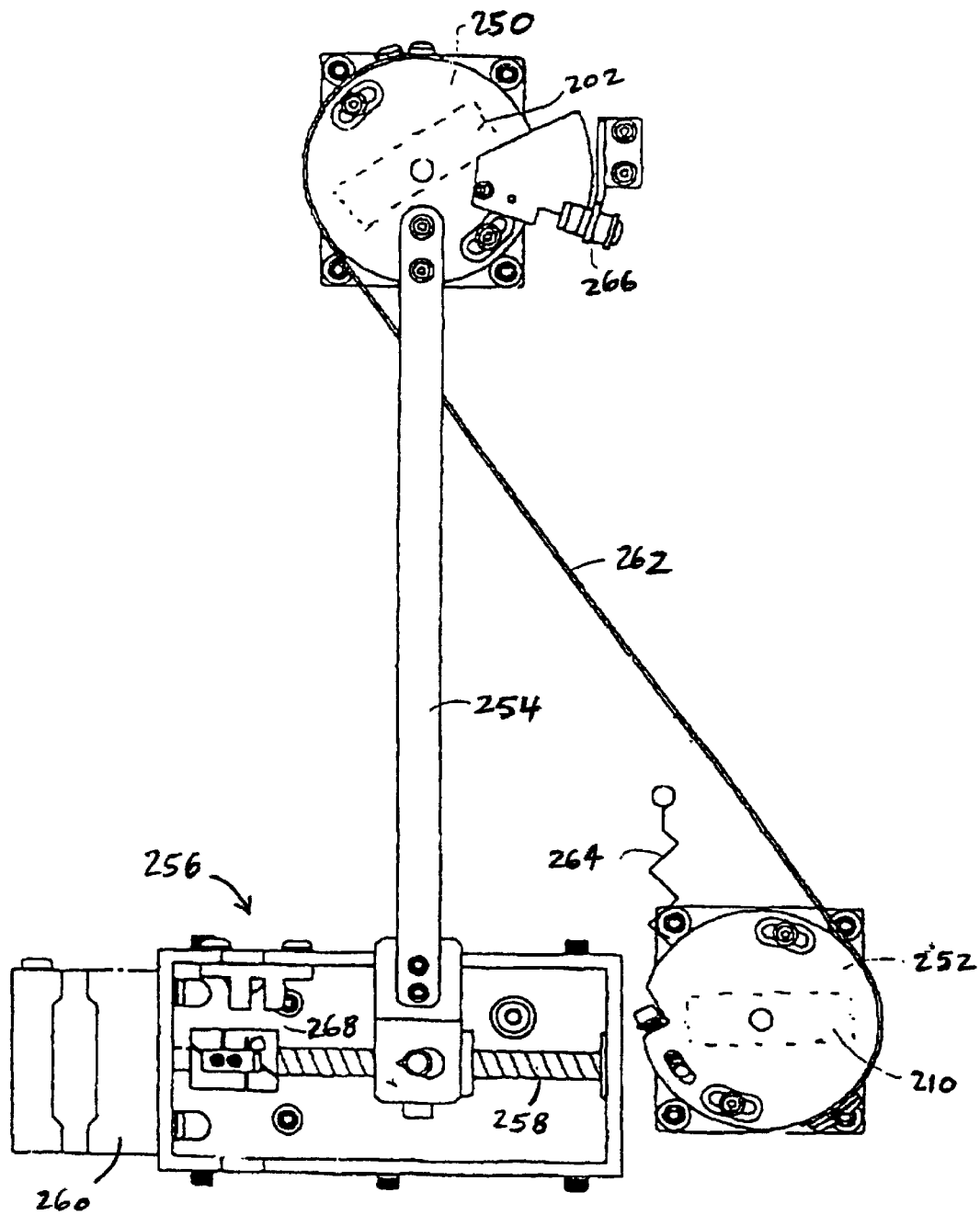
FIG. 2B is a schematic diagram showing one embodiment of a tension band actuator mechanism for pivoting the gratings of the double monochromator shown in FIG. 2A.

The FIG. 2B embodiment is provided by way of example only, and not by way of limitation; it will be appreciated that alternative mechanisms exist for pivoting gratings 202,210 either synchronously or otherwise. For example, each grating 202,210 may be provided with a respective pivot mechanism such that the angular orientation of gratings 202,210 relative to each other may be independently selectable. Additionally, alternative means for coupling gratings 202, 210 for synchronous and complementary rotation are within the scope and contemplation of the present disclosure.

FIG. 3 is a schematic diagram of one embodiment of the LTM 106 shown in FIG. 1. Excitation light enters LTM 106 through an entrance aperture whereupon it is directed, either with or without one or more mirrors 300, to a coaxial excitation mirror 302. The coaxial excitation mirror 302 may be flat, or include appropriate curvature to focus or to disperse light as desired. Coaxial excitation mirror 302 is positioned to direct the excitation light directly onto the sample 108. More particularly, coaxial excitation mirror 302 may be positioned somewhat off-axis with respect to sample 108, but should be positioned so that substantially all of the excitation light strikes the sample to achieve maximum illumination.

In one application, each well of a multi-well plate can be positioned beneath the coaxial excitation mirror 302 by X-Y translation of either LTM 106, the multi-well plate, or both. In another application involving monochromators equipped with optional microscope optics, different regions of intact biological cells that have been mounted on glass slides or culture plates can be separately imaged using optical elements in the light path and by positioning the sample beneath coaxial excitation mirror 302 by X-Y-Z translation of either LTM 106, the glass slides or culture plates, or both. Fluorescence emission from one or more fluorophores in a sample may be collected by a coaxial emission mirror 304. Coaxial emission mirror 304 may be concave so as to focus and direct the emission light, either directly or by one or more light directing mirrors 306, out of an exit port or aperture of LTM 106. In the embodiment shown in FIG. 3, emission light exits LTM 106 from the same side that excitation light enters LTM 106. However, different placements of the entrance and exit apertures may be used by suitable placement of light directing mirrors 300, 306.

In this context, "coaxial" generally refers to the position and orientation of mirrors 302,304 relative to an area to be illuminated (in the case of excitation mirror 302) and relative an area that is emitting fluorescent or luminescent light (in the case of emission mirror 304). The coaxial placement of excitation mirror 302 with an area to be illuminated, as well as the coaxial placement of emission mirror 304 with an area emitting light, combine to ensure that a high percentage of excitation light is directed onto the sample within a well 108, for example, and that a high percentage of the fluorescent or luminescent light emitted from the opening of well 108 is collected for analysis. In some embodiments, emission mirror 304 may be positioned slightly off-axis relative to excitation mirror 302 to avoid interference in the optical train.

In a particularly efficient embodiment, all of the mirrors within LTM 106 comprise front, or "first," surface mirrors. First surface mirrors have a reflective material, such as aluminum or other reflective metal, for example, coated onto the surface of a substrate, such as glass or ceramic; incident light is directed onto the reflective coating. Since the coating serves as the reflective surface, incident light does not penetrate the substrate as in an ordinary second surface mirror. Accordingly, such first surface mirrors are substantially more efficient than traditional second surface mirrors.

It will be understood by those of ordinary skill in the art that a number of different reflecting mirrors may be used to direct light within LTM 106, as needed. As noted above, however, it is generally desirable to minimize the number of such reflecting surfaces in order to improve efficiency of LTM 106. In the FIG. 3 embodiment, excitation mirror 302 may be an elliptical mirror approximately 6×9 millimeters in dimension, while the emission mirror 304 may be approximately 75 millimeters in diameter. Other dimensions can be used and generally will vary with the dimensions of the overall instrument.

Figure 4:
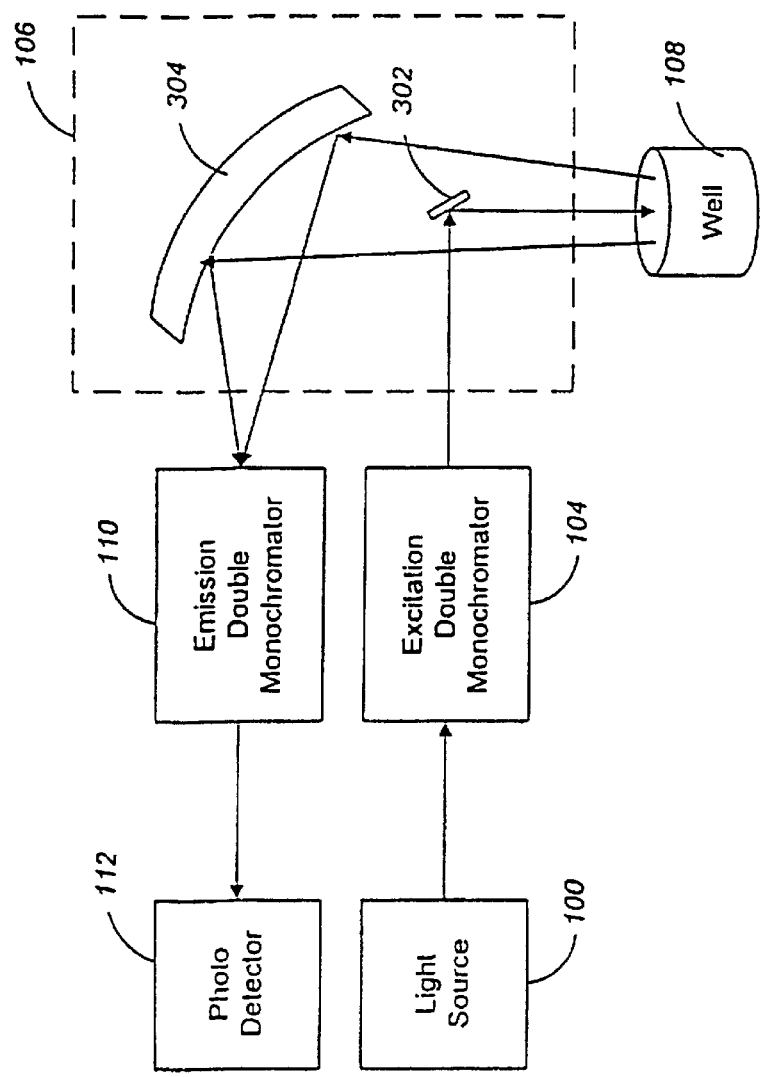
FIG. 4 is a schematic diagram of a simplified version of a fluorescence spectrophotometer constructed and operative in accordance with the present invention.

FIG. 4 is a schematic diagram of a simplified embodiment of a fluorescence spectrophotometer. As in the embodiment described above with reference to FIG. 1, excitation wavelengths may be selected from a broadband light source 100 by means of an excitation double monochromator 104. The excitation light is directed by a coaxial excitation mirror 302 to a sample within a well 108. Fluorescent and luminescent emission light may be collected and focused by a coaxial emission mirror 304 that is in reflective alignment with the coaxial excitation mirror 302. Emission mirror 304 directs the collected and focused light into an emission double monochromator 110. As described above, monochromator 110 directs one or more selected wavelengths of emission light to a photodetector and analyzer module 112 for counting and analysis. This embodiment minimizes the number of reflective surfaces within LTM 106.

The compact configuration of the embodiment shown in FIG. 4 allows for use of the instrument as a dual path spectrophotometer. That is, a sample can be illuminated with excitation light either from the open side of well 108 or from the bottom side of well 108 as set forth below.

Figure 5A:
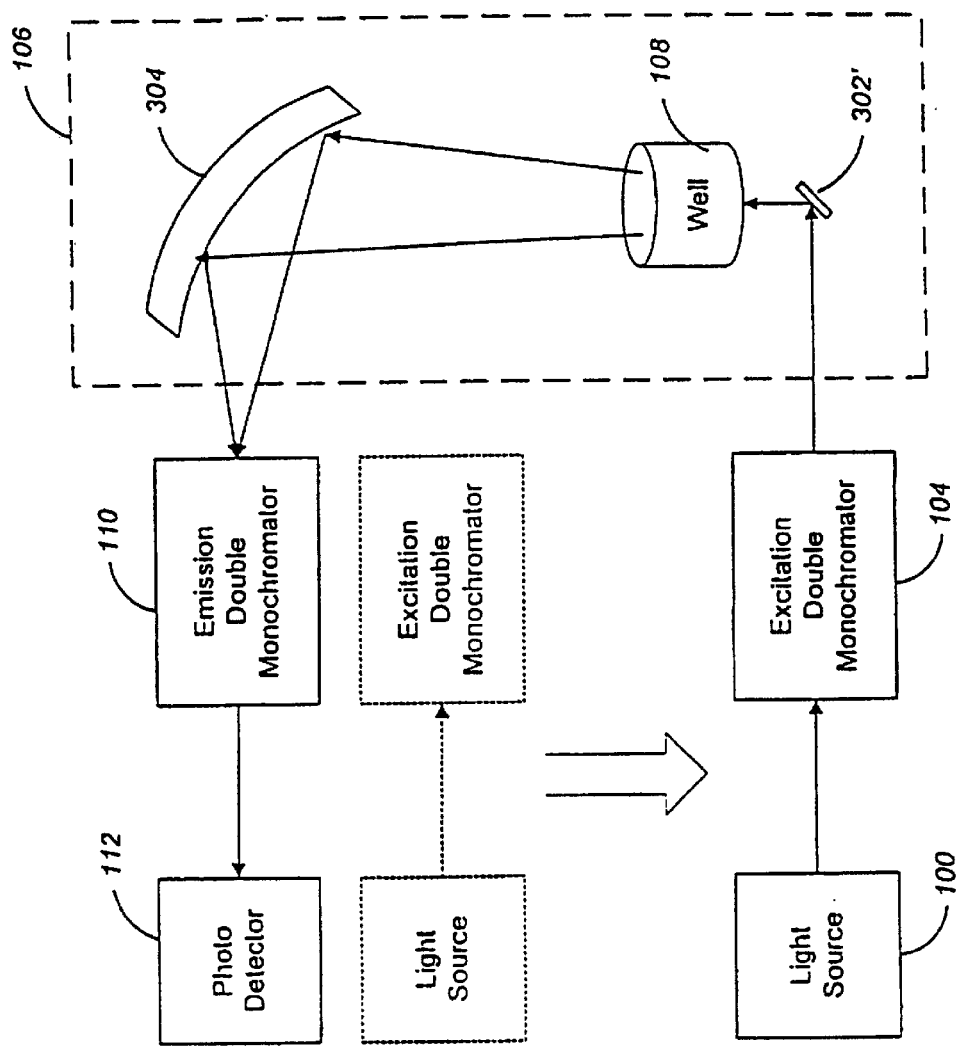
FIG. 5A shows a first alternative dual path embodiment of a fluorescence spectrophotometer system

FIG. 5A shows a first alternative dual path embodiment of a fluorescence spectrophotometer system One or both of the light source 100 and the excitation double monochromator 104 optionally may be translated from a first position (illustrated in FIG. 5A by dashed lines) to a position below a multi-well plate such that excitation light impinges upon a bottom-illumination coaxial excitation mirror 302', which directs excitation light through the transparent bottom substrate of a well 108. Alternatively, if light source 100 is not translated, light directing mirrors may be interposed to direct light through excitation double monochromator 104. Fluorescence emissions emanating from the opening of well 108 may be collected by emission mirror 304. When the system is configured for bottom-illumination, the top-illumination excitation mirror 302 (illustrated in FIG. 4, but not shown in FIG. 5A) may be removed from the light path in order to maximize the amount of fluorescent and luminescent light collected by the emission mirror 304. Alternatively, top-illumination excitation mirror 302 can be left in place. In either case, bottom-illumination excitation mirror 302' is in direct alignment (as opposed to reflective alignment) with emissions mirror 304.

Figure 5B:
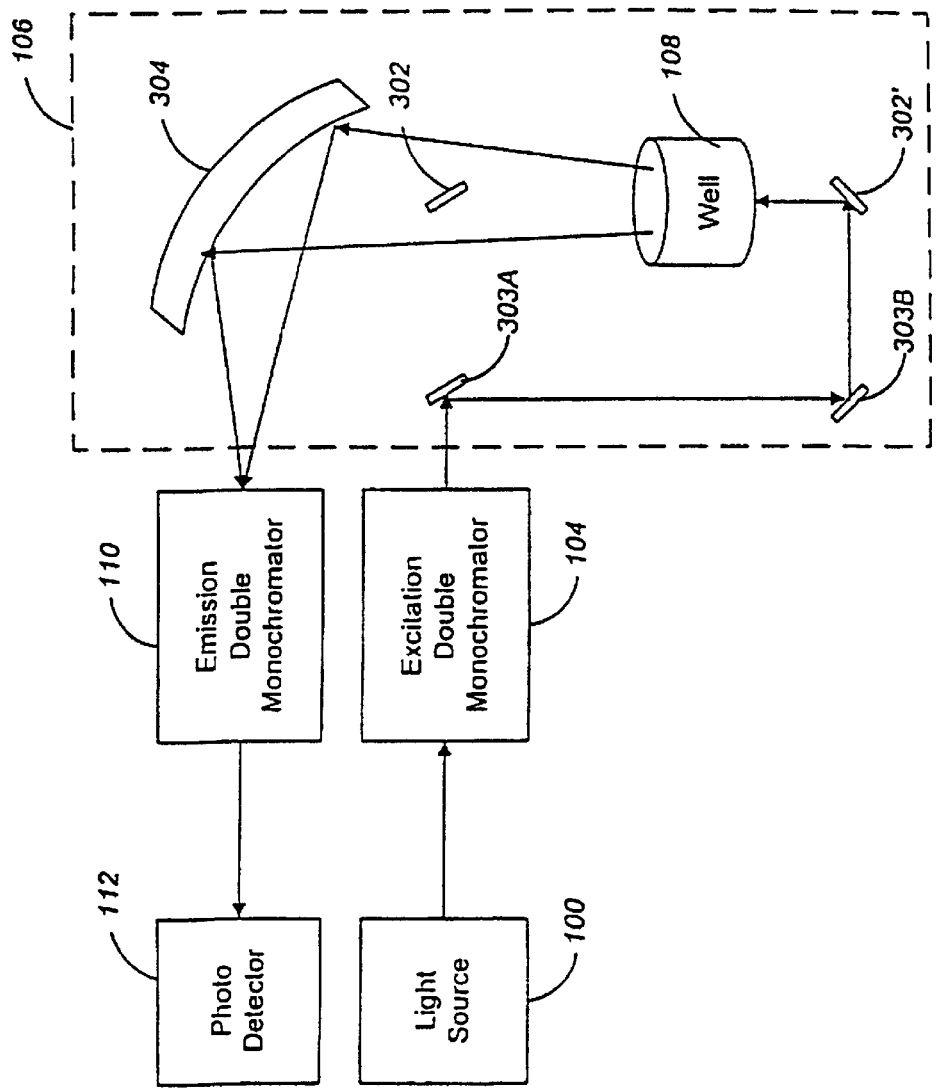
FIG. 5B shows a second alternative dual path embodiment of a fluorescence spectrophotometer system.

FIG. 5B shows a second alternative dual path embodiment of a fluorescence spectrophotometer system In this configuration implemented for bottom illumination, a set of one or more redirection mirrors 303A, 303B may be interposed into the light path from excitation double monochromator 104 in order to intercept and to direct excitation light.

The intercepted excitation light is redirected to impinge upon a bottom-illumination coaxial excitation mirror 302', which directs the excitation light through the transparent bottom substrate of well 108. The top-illumination coaxial excitation mirror 302 may be left in place, as shown, or moved out of position when the redirection mirrors 303A, 303B are moved into position. Such movement may be accomplished, for example, by translation (e.g. along an axis into or out of the page) of a carriage on which all four mirrors 302, 303A, 303B, 302', are mounted. As with the FIG. 5A embodiment, bottom-illumination excitation mirror 302' is in direct alignment (as opposed to reflective alignment) with emission mirror 304.

In all of the configurations shown in FIGS. 4, 5A, and 5B, additional redirection mirrors may be used as required to guide light to selected locations within the instrument.

According to an embodiment, a timer-counter board that operates at a frequency in excess of 100 MHz may be used. The photodetector and analyzer module (designated by reference numeral 112 in FIGS. 4, 5A, and 5B) may be configured to respond to photons at frequencies as high as 30 MHz. The dynamic range of this system ranges from 0 to more than $30 \times 10^6$ photons, thereby eliminating the dynamic range limitations which previously restricted the use of photon counting in fluorescence detection. If the observed current from the PMT is greater than a prescribed threshold established at the photodetector, a 5 volt electrical pulse having a duration of approximately 2 nanoseconds is produced; the timer-counter circuit enumerates these pulses as a function of time, that is, establishes a direct quantitation for photons per unit time.

Using a spectrophotometer according to one embodiment, a pre-cast polyacrylamide gel containing fluorescently labeled nucleic acids or proteins was placed on a flat plate in the positioning mechanism directly under the LTM. With the excitation and emission monochromators set at wavelengths suitable for the fluorescent labels, the gel was translated (in the X and Y directions) under the LTM until all of the gel area had been traversed. At each point of this travel, a fluorescent reading was made and stored as a two dimensional array representing the fluorescent emission at each point of the gel. The distance between the points was adjusted to yield the best response for a given data acquisition time. In the actual experiments, the gel was also scanned as "lanes" representing the path of electrophoresis from the sample well at the top of the gel to the base of the gel because the fluorophores in an electrophoresis gel are arrayed in a line rather than as a point. Each such lane was scanned from the sample well to the bottom of the gel to achieve a substantial reduction in overall data collection time. As a reference for background, a blank lane was scanned and the data subtracted on a point-by-point basis from the corresponding data for lanes containing fluorophores. The corrected data were then analyzed in two ways. In one analysis, an image was constructed of the original gel which was compared to standard laboratory photographs of the same gel for evaluation of standard gel parameters such as migration distance, separation of molecules, and concentration of molecular species as determined separately by the digital image and the film. In the other analysis, a "densitometry" plot equivalent to those made for gel lanes from autoradiography films using flat bed scanning detectors was created. From the database relating fluorescence intensity of a lane, the center of each fluorescent band was identified and a cross sectional graph of fluorescent intensities as a function of migration distance was prepared. From the use of gels prepared with different but known amounts of the same fluorescent labeled nucleic acids, a standard curve establishing lower and upper limits of sensitivity, resolution, and overall dynamic range for gel detection were determined.

The "square intensity point spread function" and the "long penetration depth" properties of one and two photon absorption processes have been recognized as important features in future developments in fluorescence detection. Both are accomplished by focusing a femtosecond short pulse laser onto a focal plane in a sample to be studied for fluorescence. In a spectrophotometer according to another embodiment, a laser beam from an appropriate laser was substituted for the quartz halogen or xenon light source used for excitation. The laser beam was used to illuminate the entrance aperture of the excitation monochromator. Additional modifications where needed in some cases including, for example, the use of one or two pinhole apertures rather than the standard rectangular slits, and the insertion of an objective lens to focus the light after it had passed through the monochromator. The fluorescence emission was collected through the light transfer module as previously and the fluorescence measured as a function of time, or in the cases of image formation and area scanning, as a function of time and position of the light transfer module over the sample as described in the gel analysis above. In this configuration, a pinhole exit aperture on the excitation monochromator was used to image light onto a sample, and each point of the image used to excite fluorescence. Moving the sample position in an x-y-z fashion enabled scanning of areas of the sample to create an image or database. For confocal microscopy, two pinhole apertures were required as described below. For multi-photon applications, only a single pinhole aperture was used as the exit aperture of the excitation monochromator. For two-photon excitation, a microlens array could be used if needed to focus the beam for high transmittance. In general, the configuration was epi-fluorescent although in certain polarization applications, excitation was from the bottom and emission light was collected from the top.

In yet another embodiment, a fluorescence spectrophotometer system constructed and operative in accordance with the present invention was applied in the creation of a scanning fluorescence polarization detector. Fluorescent molecules in solution, when excited with plane polarized light, will emit light back into a fixed plane (i.e. the light remains polarized) if the molecules remain stationary during the fluorophore's period of excitation (excited state lifetime). Molecules in solution, however, tumble and rotate randomly, and if the rotation occurs during the excited state lifetime and before emission occurs, the planes into which light is emitted can be very different from the plane of the light used for the original excitation.

The polarization value of a molecule is proportional to its rotational relaxation time, which by convention is defined as the time required for a molecule to rotate through an angle of 68.5°. Rotational relaxation time is related to solution viscosity ($\eta$), absolute temperature (T), molecular volume (V), and the gas constant (R):

$$\text{Polarization value} \propto \text{Rotational Relaxation Time} = 3\eta V/RT$$

Figure 6:
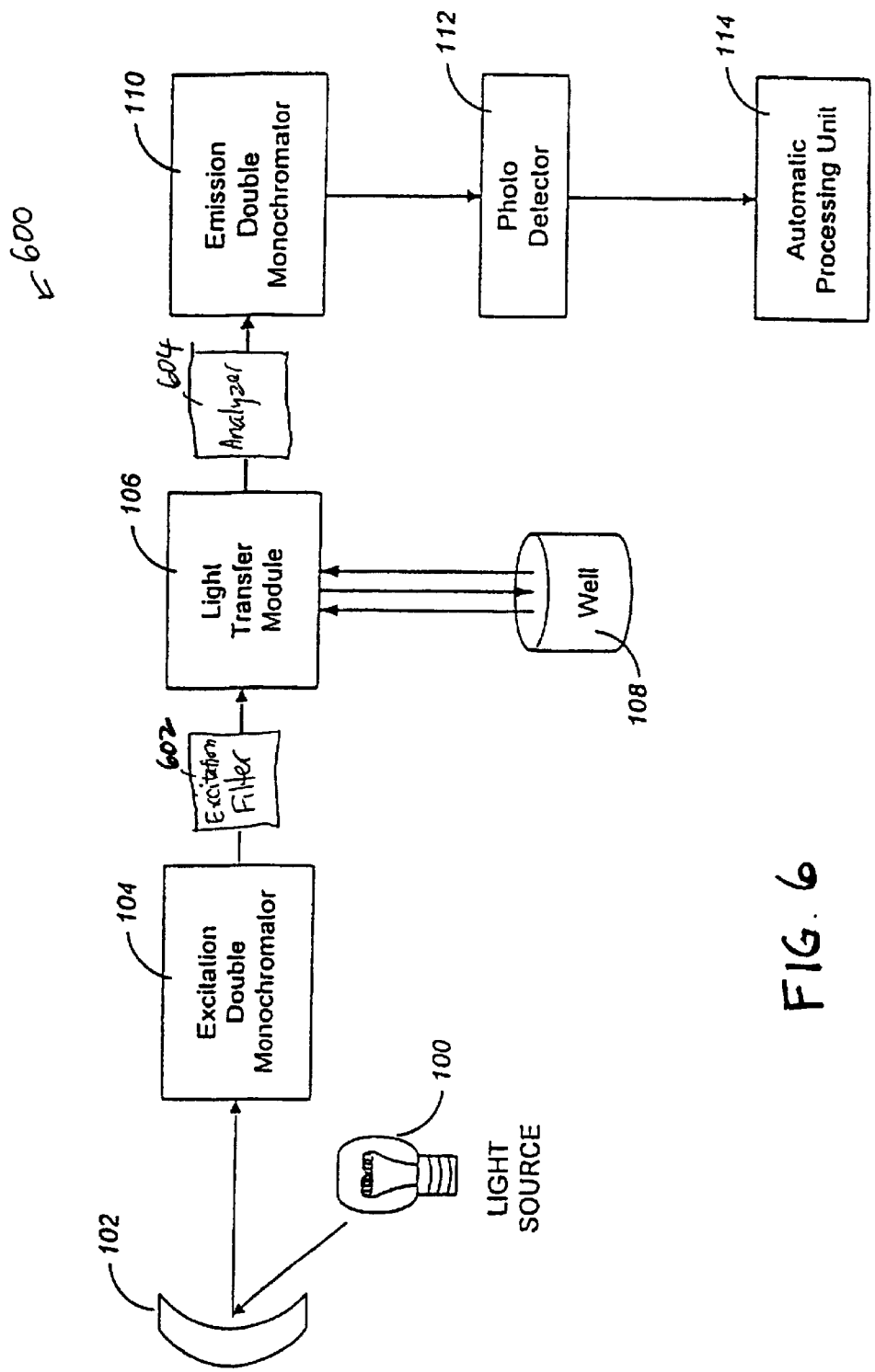
FIG. 6 is a schematic diagram of an embodiment of a fluorescence spectrophotometer system including fluorescence polarization.

If viscosity and temperature are constant, the polarization is directly related to molecular volume (molecular size), which, in general, correlates well with molecular weight. Changes in molecular volume result from several causes, including degradation, denaturation, conformational changes, or the binding or dissociation of two molecules. Any of these changes can be detected as a function of changes in the polarization value of a solution. Specifically, a small fluorescent molecule which rotates freely in solution during its excited state lifetime can emit light in very different planes from that of the incident light. If that same small fluorophore binds to a larger molecule, the rotational velocity of the small molecule decreases and the effect is detected as a decrease in the polarization value. Measurement of the effect requires excitation by polarized light which can be obtained using a laser or through light selection using a polarizing filter which only transmits light traveling in a single plane. In one experiment, light of a defined wavelength obtained from one embodiment of an excitation monochromator operative in accordance with the present invention was further refined by passing the light through a polarizing filter (designated the "polarizer") to obtain monochromatic, plane polarized light for excitation (for the present purposes designated "vertically polarized light"). Concurrently, the light path for collecting the emission light was similarly modified by selective introduction of one of a pair of polarizing filters (designated the "analyzers"), one of which can be rotated to a position vertical to the plane of the excitation light, whereas the other of which can be rotated to a position horizontal to the plane of the excitation light. When a fluorescent sample in solution was introduced into the light path between the polarizer and the analyzers, only those molecules which were oriented properly to the vertically polarized plane absorbed light, became excited, and subsequently emitted light. By selecting the appropriate analyzing filter to be inserted into the emission light path, the amount of emitted light in the vertical and horizontal planes can be measured and used to assess the extent of rotation of the small fluorescent molecule in the solution before and after binding to a larger molecule. FIG. 6, described below, illustrates a system which may facilitate the forgoing experiment.

In yet another application, a fluorescence spectrophotometer system was utilized in confocal microscopy—a method for eliminating one of the fundamental difficulties of fluorescence microscopy, namely, the reduction in spatial resolution at the focal plane of the microscope owing to out-of-focus light. A spectrophotometer according to another embodiment was used to create a confocal microscope from the embodiment essentially as described under laser excitation above to focus a light image on whole cell mounts and to achieve both multiple and single photon excitation of the fluorescent labels in a sample. Fluorophores in planes out of the focus were not illuminated and did not fluoresce.

In confocal imaging, apertures were used in both the excitation and emission light paths in order to focus a cone of light through the specimen and in the emission light path in order to eliminate scattered and out-of-plane fluorescence. The development of mode locked dye lasers has made simultaneous multi-photon excitation practical because such lasers are capable of delivering the available excitation energy to a focal spot in very brief pulses and with sufficient energy to achieve two photon excitation. In multi-photon imaging, the focal spot provided by the laser excites a sufficiently small volume that, when used in conjunction with the light transmission module described above, makes it possible to collect all emission light without a second pinhole aperture on the emission side. No emission aperture changes were necessary.

FIG. 6 is a schematic diagram of an embodiment of a fluorescence spectrophotometer system including fluorescence polarization as noted briefly above. In the FIG. 6 embodiment, light exiting the excitation monochromator 104 may be plane polarized In that regard, an excitation polarizing filter 602 may be operative to polarize the excitation light in a selected orientation. The polarized excitation light is transferred to the sample well 108 via LTM 106. Resulting fluorescent and luminescent light emitted by the sample is collected by LTM 106, which directs emission light to a polarization analyzer 604. In operation, polarization analyzer 604 may determine if the light emitted from well 108 has been rotated from its original orientation 602. Such rotation may provide information about the sample in well 108, for example, the spin and/or size of molecules in the sample. Analyzer 604 transmits the emission light to the entrance aperture of emission double monochromator 110 as described above with reference to the embodiment shown in FIG. 1.

Excitation polarizing filter 602 may generally be implemented as an optical filter operative to restrict the excitation light to plane polarized excitation light oriented in a selected plane, as is generally known in the art. An optical filter holder (not shown) may be employed selectively to insert the optical polarizing filter 602 into the path of the excitation light.

Figure 7:
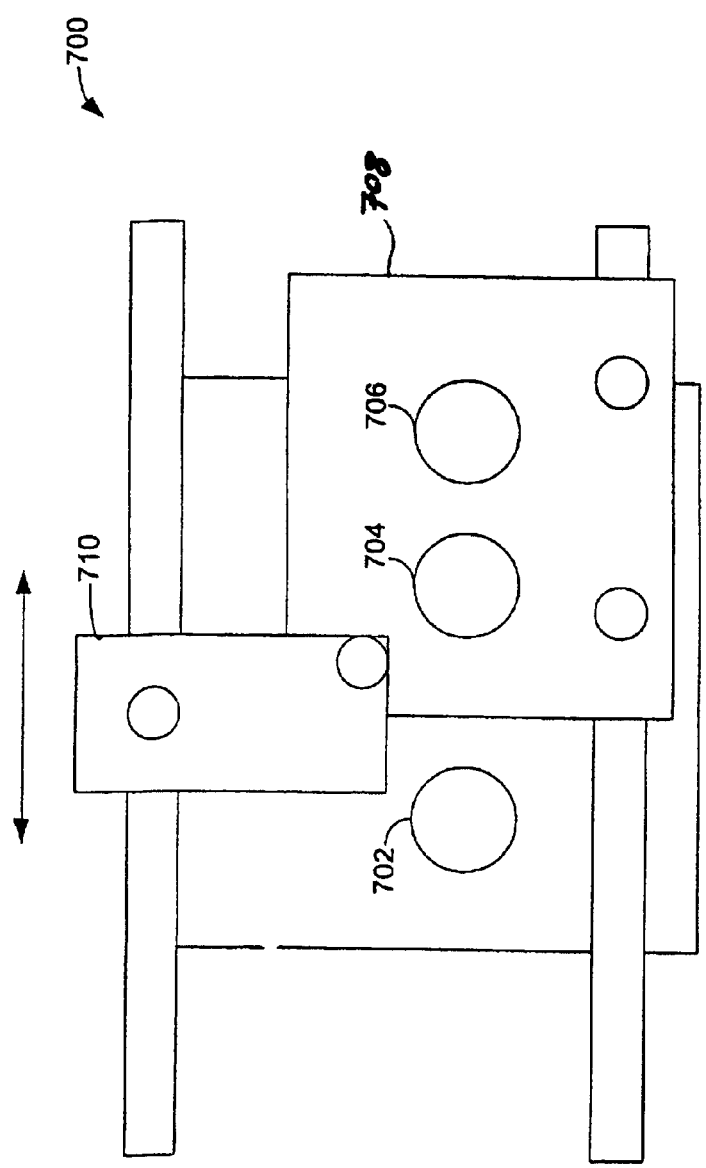
FIG. 7 is a simplified diagrammatic view of one embodiment of a polarization analyzer constructed and operative in accordance with one embodiment of the present invention.

FIG. 7 is a simplified diagrammatic view of one embodiment of a polarization analyzer 700 constructed and operative in accordance with one embodiment of the present invention. Analyzer 700 generally corresponds, to and incorporates all of the functionality of, analyzer 604 described above with reference to FIG. 6. Analyzer 700 may include an aperture 702 operative to admit emission light (from LTM 106 as indicated in FIG. 6) and two emission polarizing filters 704 and 706, which may be disposed on a filter holder such as plate 708, for example. A first emission polarizing filter 704 has a polarization parallel to that of the excitation polarization filter 602, and hence passes light having the original orientation produced by the excitation polarizing filter 602. A second emission polarizing filter 706, on the other hand, has a polarization perpendicular to that of excitation polarizing filter 602, and hence blocks light having the original orientation. A motorized slider 710 or other suitable mechanism may slide filter plate 708 between two positions: a first position in which the first (parallel) polarization filter 704 is aligned with aperture 702 in the light train, and a second position in which the second (perpendicular) polarization filter 706 is aligned with aperture 702 in the light train.

Two measurements may be taken for each sample. For the first measurement, the motorized slider 710 slides the filter plate 708 into the first position and any emission fluorescence from the sample may be passed through the parallel filter 704. For the second measurement, the motorized slider 710 slides the filter plate into the second position, and any emission fluorescence from the sample may be passed through the perpendicular filter 706. The amount of rotation, if any, may be determined by comparing the two measurements. For example, if the polarization of the excitation light has not been rotated in the sample, no emission fluorescence should be detected in the second measurement, since all of the light in the original orientation would be blocked by the perpendicular filter 706.

Though polarization analyzer 700 has been illustrated and described as a discrete component (e.g. reference numeral 604 in FIG. 6) of a fluorescence spectrophotometer system, it will be appreciated that the components detailed in FIG. 7 or their equivalents, as well as the polarization analyzer functionality, may alternatively be incorporated into the emission side of LTM 106 or into monochromator 110 illustrated in FIG. 6. As set forth in detail below, some embodiments incorporate emission polarization analyzer functionality in the LTM upstream of the emission mirror in the light train. Similarly, an excitation polarizing filter (reference numeral 602 in FIG. 6) may be incorporated into monochromator 104 or the excitation side of LTM 106.

Figure 8:
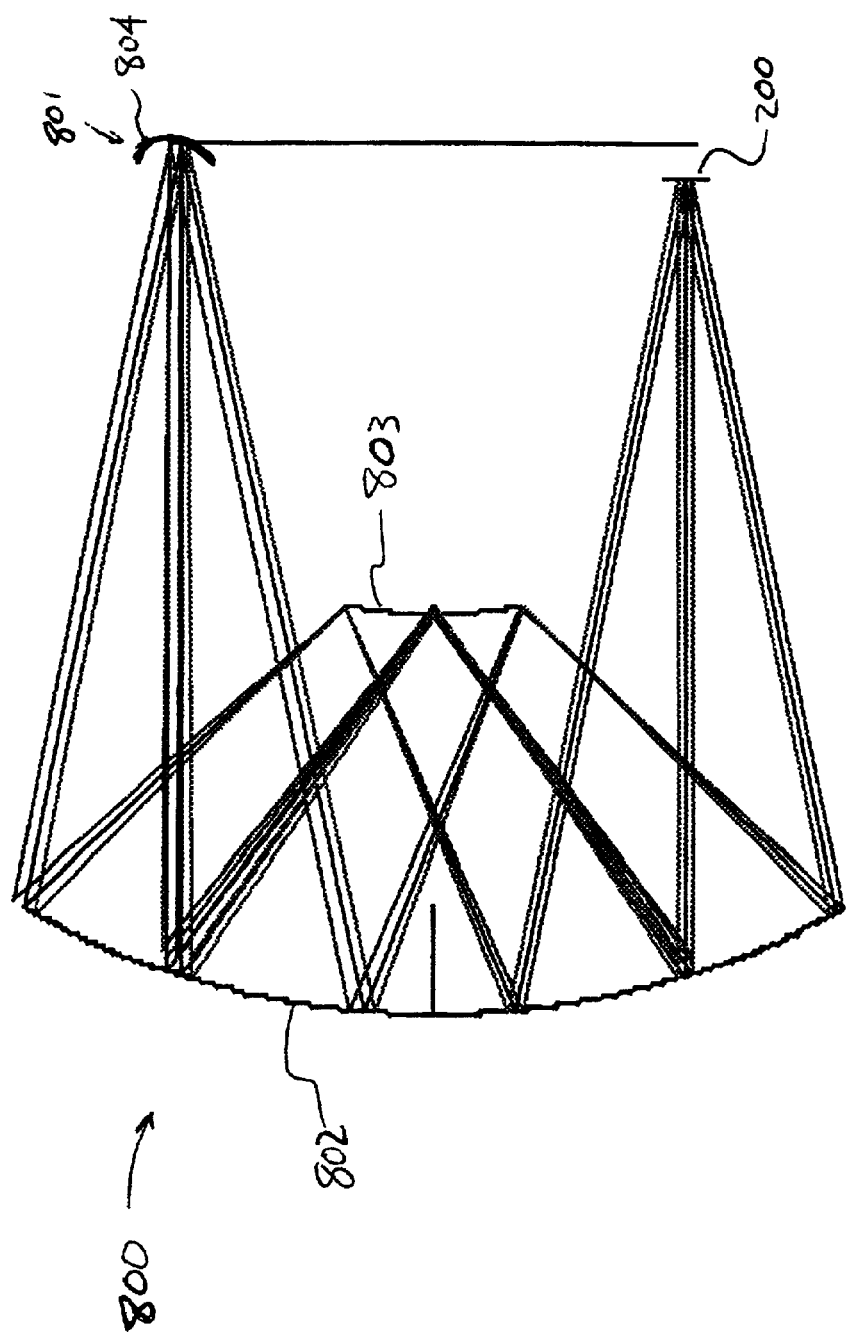
FIG. 8 is a simplified cross-sectional diagram of an illumination system

FIG. 8 is a simplified cross-sectional diagram of an illumination system Illumination system 800 may generally correspond to light source 100 illustrated in FIGS. 4, 5A, and 5B. Illumination system 800 may be operative to image the filament of a light source or lamp 801 onto the entrance aperture 200 of an excitation monochromator such as represented by reference numeral 104 in FIG. 1. In the FIG. 8 embodiment, a first spherical reflection surface 802 and a second spherical reflection surface 803 cooperate to form a spherical concave reflector system, in this case an Offner 1:1 afocal relay. Spherical surfaces 802,803 may be used to correct for all third order aberrations; the spherical concave reflector system is telecentric at both ends of the optical train.

As is generally known in the art, lamp 801 may include a rear mirror 804 operative to reflect the flux from the rear of the filament forward through the system. Additionally or alternatively, an aperture wheel having interchangeable apertures (not shown) may be inserted into the light path. Rotation of the aperture wheel enables selection of one of a plurality of apertures to be inserted into the light path illustrated in FIG. 8, for example; accordingly, the cone angles of the flux incident on entrance aperture 200 may be selectively adjusted in accordance with system requirements.

In that regard, means for selectively inserting one of a plurality of apertures into the path of light moving through the spherical concave reflector system of illumination source 800 may be included. Mechanisms such as linear actuators, gears for rotating an aperture wheel, and the like are contemplated. Various methods of interposing one or more apertures into an optical train are known in the art.

FIG. 9 is a simplified cross-sectional diagram of one embodiment of a light transfer module incorporating a compound parabolic concentrator. As indicated by the arrow in FIG. 9, excitation light may be admitted to LTM 106 (generally represented by the dashed lines in FIG. 9) from the left side of the diagram, and is directed through an aperture 902 by excitation mirror 302 (see FIGS. 4, 5A, and 5B), which is appropriately mounted as shown, to illuminate a sample. A compound parabolic concentrator (CPC) 901 may receive emission light (i.e. fluorescent or luminescent light emitted from the illuminated area containing sample) through aperture 902.

In accordance with this embodiment, CPC 901 may comprise a polished, reflective surface operative to collect the flux radiated from the illuminated sample and to concentrate emission light for reflection by an emission mirror (not shown in FIG. 9) such as described in detail above.

As noted above, the various components of the emission polarization analyzer (see FIGS. 6 and 7) may be interposed between CPC 901 and the emission mirror, incorporating the functionality of a polarization analyzer into LTM 106. This arrangement may substantially reduce the influence of the LTM 106 itself on the polarization state of the emission light.

Figure 10A:
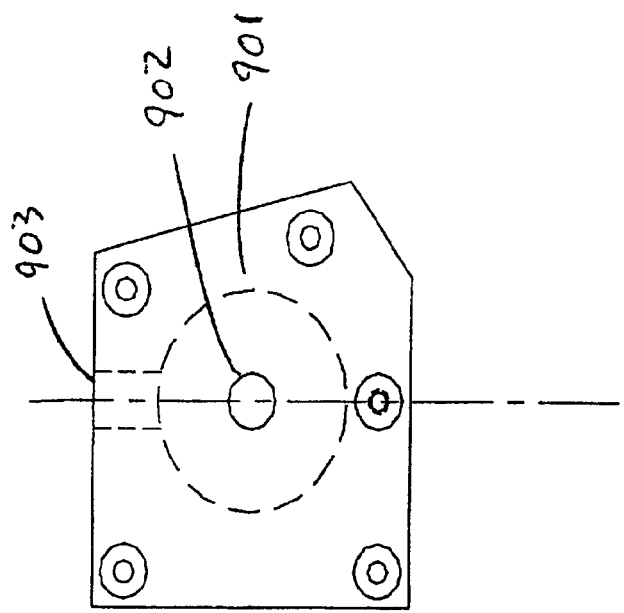
FIG. 10A is a simplified cross-sectional diagram of the interior of a light transfer module incorporating a compound parabolic concentrator.
Figure 10B:
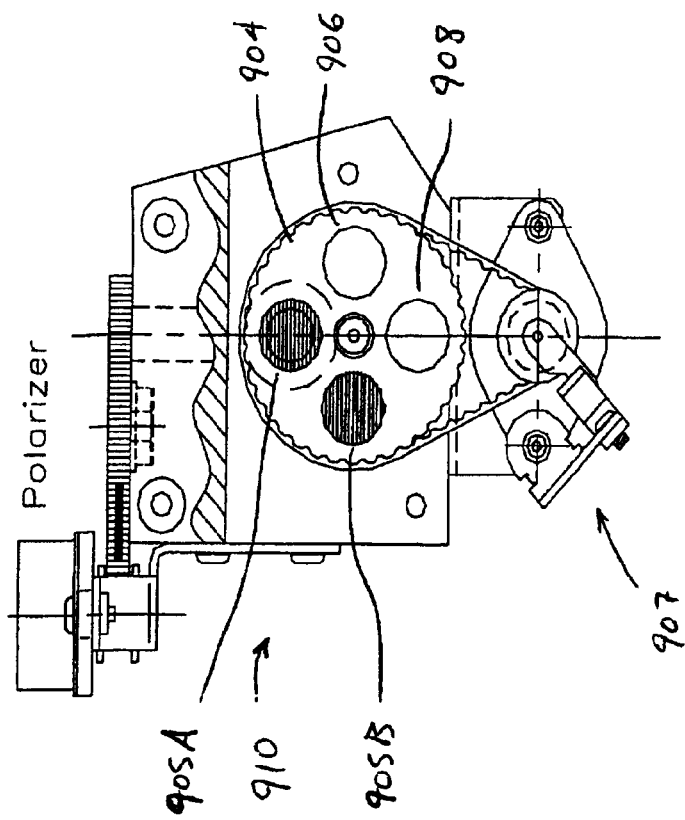
FIG. 10B is a simplified cross-sectional diagram of one embodiment of a light transfer module incorporating emission polarization upstream of an emission mirror.

FIG. 10A is a simplified cross-sectional diagram of the interior of a light transfer module incorporating a compound parabolic concentrator, and FIG. 10B is a simplified cross-sectional diagram of one embodiment of a light transfer module incorporating emission polarization upstream of an emission mirror. The views depicted in FIGS. 10A and 10B are parallel to the light train and are taken at lines 10A and 10B, respectively, shown in FIG. 9; i.e. emission light directed through aperture 902 of CPC 901 in FIG. 10A passes through the polarizer unit 910 in FIG. 10B before being directed by an emission mirror to an emission double monochromator as described above.

In the FIG. 10A embodiment, an aperture 903 admits excitation light from an excitation double monochromator into LTM 106 as described above with reference to FIG. 9. As noted above, emission light emitted by the illuminated sample passes through aperture 902 and is directed by the polished interior surface of CPC 901 to an emission mirror.

Polarizer unit 910 illustrated in FIG. 10B may be interposed between CPC 901 and an emission mirror, such that emission light may be polarized or otherwise filtered before it impinges on the emission mirror. In operation, an actuator or drive motor 907, for example, coupled to a filter holder or wheel 904 may enable selection of one of a plurality of polarizing filters (represented by reference numerals 905A and 905B) or other filters (represented by reference numeral 906). One or more slots (represented by reference numeral 908) in wheel 904 may be provided with no filter at all. Accordingly, a filter holder such as wheel 904 may be selectively operative to insert one of a plurality of polarizing or other filters into the path of the emission light. The quantity, nature, and polarization plane of the various filters incorporated in wheel 904 may be selected as a function of overall system requirements.

It will be appreciated that alternative or additional mechanisms may be implemented to enable selection of filters in polarizer unit 910. Linear translation of a filter plate such as described above with reference to FIG. 7, for example, may be appropriate and equally effective, depending upon size and operational requirements of the LTM in the context of the overall spectrophotometer system.

It will also be appreciated that the foregoing descriptions of the drawing figures are exemplary only, and that the disclosed embodiments are susceptible to modifications and alterations which may improve overall system efficiency. For example, rotating aperture wheels and appropriate mountings may additionally be implemented in the LTM 106 of FIG. 9; apertures may be selected in accordance with the dimensions of a sample well, for instance, to adjust excitation light passed through aperture 902 such that stray light may be minimized.

In one embodiment of a double monochromator such as depicted in FIG. 2A, for example, baffles may be incorporated to reduce stray light originating from diffracted flux which does not pass through the first selection aperture 206. Spectroradiometer measurements of monochromator designs without baffles have revealed that considerable flux which is half the desired wavelength may be transmitted through the first selection aperture; for example, if a conventional excitation monochromator is set to pass light having a wavelength of 600 nm, then flux having a wavelength of 300 nm may also be transmitted through the selection aperture as second order aberrations. Accordingly, reduction of stray light through implementation of baffles may represent an important determinant with respect to the purity of the light output by the monochromator.

Figure 11:
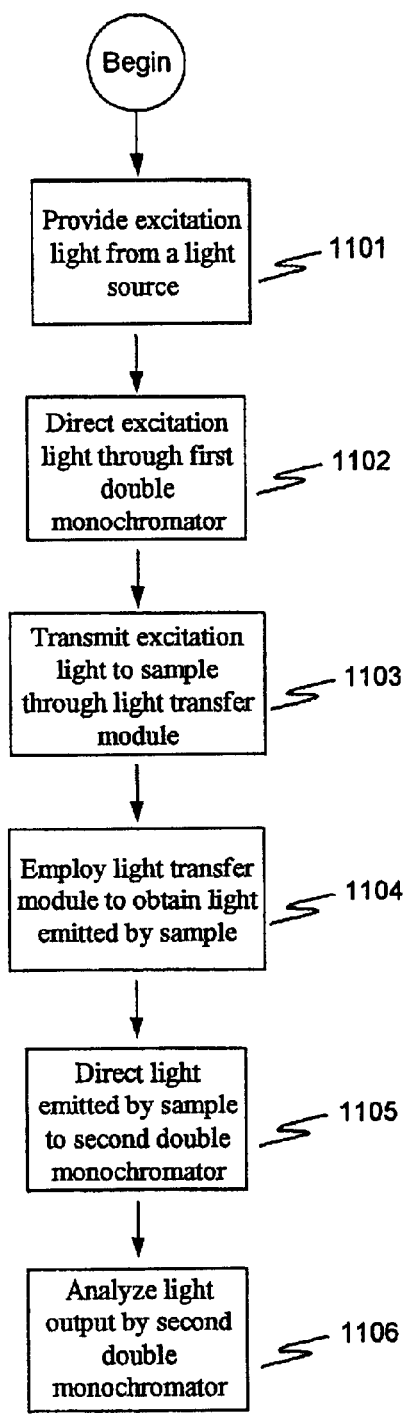
FIG. 11 is a simplified flow diagram illustrating one embodiment of a method of analyzing a sample.

FIG. 11 is a simplified flow diagram illustrating one embodiment of a method of analyzing a sample. As set forth in detail above with reference to the system embodiments, a method of analyzing a sample generally comprises providing excitation light from a light source (block 1101), directing the excitation light through a first double monochromator (block 1102), transmitting the excitation light to the sample through a light transfer module(block 1103), employing the light transfer module to obtain light emitted by the sample (block 1104), directing the light emitted by the sample to a second double monochromator (block 1105), and analyzing light output by the second double monochromator (block 1106). As noted above, the FIG. 11 embodiment may be employed to detect and to analyze more than one fluorescent compound in a single sample.

Several features and aspects of the present invention have been illustrated and described in detail with reference to particular embodiments by way of example only, and not by way of limitation. Those of skill in the art will appreciate that alternative implementations and various modifications to the disclosed embodiments are within the scope and contemplation of the invention. For example, the disclosed double monochromators may be implemented in other types of instruments, and the LTM may be employed in filter-based spectrophotometers or other optical instruments. As a further example, the LTM may be used to direct input light to an area to be illuminated, and efficiently to collect, focus, and direct light emitted (e.g. either by reflection or by fluorescence) from the illuminated area. Accordingly, it is intended that the invention be considered as limited only by the scope of the appended claims.

What is claimed is:

1. A fluorescence spectrophotometer system comprising:
    a light source;
    a first double monochromator comprising two or more gratings and operative to separate light from the light source into a plurality of wavelengths and to output selected wavelengths as excitation light;
    a light transfer module comprising a first reflection surface and a second reflection surface, the first and second reflection surfaces substantially centered on a common axis, wherein:
        the first reflection surface operates to direct substantially all of the excitation light directly onto a sample located within an area to be illuminated, the illuminated area centered on the common axis at a point between the first and second reflection surfaces; and
        the second refection surface operates to direct light that is emitted from the sample as fluorescent or luminescent light;
    a second double monochromator comprising two or more gratings and operative to separate the fluorescent or luminescent light directed by the light transfer module into a plurality of wavelengths and to output selected wavelengths of the fluorescent or luminescent light as emission light; and
    a photodetector and analyzer, operative to receive the emission light output by the second double monochromator, to detect the selected wavelengths of the emission light, and to output an indication of the selected wavelengths.

2. The system of claim 1 wherein at least one of the first double monochromator or the second double monochromator comprises:
    an entrance aperture for accepting light;
    a first optical grating positioned to disperse at least part of the light accepted through the entrance aperture;
    a first selection aperture positioned to intercept part of the light dispersed by the first optical grating and operative to pass selected wavelengths of the dispersed light;
    a second optical grating positioned to disperse at least part of the light passed through the first selection aperture; and
    a second selection aperture positioned to intercept part of the light dispersed by the second optical grating and operative to pass selected wavelengths of the dispersed light.

3. The system of claim 2 wherein the first optical grating and the second optical grating are concave.

4. The system of claim 3 wherein the first optical grating and the second optical grating are holographic concave gratings.

5. The system of claim 2 wherein each of the first optical grating and the second optical grating is operative to pivot about a respective axis of rotation allowing selection of a range of wavelengths of light to be passed through the first selection aperture and the second selection aperture, respectively, as a function of rotation angle.

6. The system of claim 5 further comprising means for pivoting the first optical grating about its respective axis of rotation and pivoting the second optical grating about its respective axis of rotation synchronously.

7. The system of claim 6 wherein the means for pivoting comprises a band drive mechanism operatively coupled to each of the first optical grating and the second optical grating.

8. The system of claim 1 wherein the first reflection surface is an excitation mirror positioned substantially coaxial with a well containing the sample and wherein the second reflection surface is an emission mirror positioned substantially coaxial with the well containing the sample.

9. The system of claim 8 wherein the first reflection surface is a parabolic first-surface excitation mirror operative to focus the excitation light directly onto the sample.

10. The system of claim 8 wherein the emission mirror is a spherical mirror.

11. The system of claim 8 wherein the excitation mirror and the emission mirror are first-surface mirrors.

12. The system of claim 8 wherein the excitation mirror is positioned to direct the excitation light into the opening of a selected well in a microwell plate containing as many as 5000 discrete microwells.

13. The system of claim 8 wherein the well includes a transparent bottom substrate and a top opening, and wherein:
    the excitation mirror is positioned to direct the excitation light into the well through the transparent bottom substrate and the emission mirror is positioned to collect the emission light from the top opening of the well.

14. The system of claim 13 wherein at least one of the light source or the first double monochromator is operative to direct the excitation light directly onto the excitation mirror.

15. The system of claim 13 further comprising a light directing mirror operative to direct excitation light from the first double monochromator to the excitation mirror.

16. The system of claim 1 wherein the photodetector and analyzer counts the number of photons of the selected wavelengths of the emission light.

17. The system of claim 1 further comprising:
    an optical filter operative to restrict the excitation light to plane polarized excitation light; and
    an optical filter holder selectively operative to insert the optical filter into the path of the excitation light.

18. The system of claim 17 wherein the optical filter and the optical filter holder are incorporated into the first double monochromator.

19. The system of claim 17 wherein the optical filter and the optical filter holder are incorporated into the light transfer module.

20. The system of claim 17 further comprising:
    a first polarizing filter operative to transmit emission light in a plane which is parallel to the plane of the polarized excitation light;

a second polarizing filter operative to transmit emission light in any plane which is not parallel to the plane of the polarized excitation light; and a polarizing filter holder selectively operative to insert one of the first polarizing filter or the second polarizing filter into the path of the emission light.

21. The system of claim 20 wherein the first polarizing filter, the second polarizing filter, and the polarizing filter holder are incorporated into the second double monochromator.

22. The system of claim 20 wherein the first polarizing filter, the second polarizing filter, and the polarizing filter holder are incorporated into the light transfer module.

23. A double monochromator comprising:

an entrance aperture for accepting input light;

a first optical grating positioned to disperse at least part of the light accepted through the entrance aperture;

a first selection aperture positioned to intercept part of the light dispersed by the first optical grating and operative to pass a selected range of wavelengths of the dispersed light;

a second optical grating positioned to disperse at least part of the light passed through the first selection aperture; and a second selection aperture positioned to intercept part of the light dispersed by the second optical grating and operative to pass a selected range of wavelengths of the dispersed light as output light;

wherein each of the first optical grating and the second optical grating is operative to pivot about a respective axis of rotation allowing selection of a range of wavelengths of light to be passed through the first selection aperture and the second selection aperture, respectively, as a function of rotation angle;

the double monochromator further comprising means for pivoting the first optical grating about its respective axis of rotation and pivoting the second optical grating about its respective axis of rotation synchronously; and wherein the means for pivoting comprises a band drive mechanism operatively coupled to each of the first optical grating and the second optical grating.

24. The double monochromator of claim 23 further comprising:

an optical filter operative to restrict the output light to a selected polarized plane; and an optical filter holder selectively operative to insert the optical filter into the path of the output light.

25. The double monochromator of claim 23 wherein the input light is polarized; the double monochromator further comprising:

a first polarizing filter operative to transmit light in a plane which is parallel to the plane of the polarized input light;

a second polarizing filter operative to transmit light in any plane which is not parallel to the plane of the polarized input light; and a polarizing filter holder selectively operative to insert one of the first polarizing filter or the second polarizing filter into the path of the input light.

26. A light transfer module comprising:

an excitation mirror operative to direct incoming light arriving at the light transfer module from a light source wherein the excitation mirror is operative to illuminate an area such that the illuminated area emits fluorescent or luminescent light; and an emission mirror operative to focus and to direct light emitted by the illuminated area as emission light, wherein the excitation mirror, the emission mirror and the illuminated area are substantially centered along a common axis.

27. The light transfer module of claim 26 wherein the emission mirror is a spherical mirror.

28. The light transfer module of claim 26 wherein the excitation mirror and the emission mirror are first-surface mirrors.

29. A light transfer module comprising:

an excitation mirror operative to direct incoming light to illuminate an area such that the illuminated area emits fluorescent or luminescent light;

an emission mirror operative to focus and to direct light emitted by the illuminated area as emission light;

an optical filter operative to restrict the incoming light to a selected polarized plane; and an optical filter holder selectively operative to insert the optical filter into the path of the incoming light, wherein the excitation mirror, the emission mirror and the illuminated area are substantially centered along a common axis.

30. The light transfer module of claim 29 further comprising:

a first polarizing filter operative to transmit light in a plane which is parallel to the plane of the polarized incoming light;

a second polarizing filter operative to transmit light in any plane which is not parallel to the plane of the polarized incoming light; and a polarizing filter holder selectively operative to insert one of the first polarizing filter or the second polarizing filter into the path of the emission light.

31. The light transfer module of claim 30 wherein the polarizing filter holder is selectively operative to interpose one of the first polarizing filter or the second polarizing filter between the illuminated area and the emission mirror.

32. A spectrophotometer system comprising:

a light source comprising a spherical concave reflector system; the reflector system being telecentric at both ends and fully corrected for third order aberrations;

a first multiple-grating monochromator having an entrance aperture; the first multiple-grating monochromator being operative to separate light imaged onto the entrance aperture from the light source into a plurality of wavelengths and to output selected wavelengths as excitation light;

a light transfer module comprising:
    a first reflection surface operative to direct substantially all of the excitation light directly onto a sample; and
    a second reflection surface in alignment with the first reflection surface; the second reflection surface being a compound parabolic reflective surface and operative to collect and to direct light emitted from the sample as fluorescent or luminescent light, wherein the first reflection surface, the second reflection surface and an area to be illuminated are centered on a common axis;

a second multiple-grating monochromator operative to separate the fluorescent or luminescent light into a plurality of wavelengths and to output selected wavelengths of the fluorescent or luminescent light as emission light; and a photodetector and analyzer, operative to receive the emission light output by the second multiple-grating monochromator, to detect the selected wavelengths of the emission light, and to output an indication of the selected wavelengths.

33. The system of claim 32 wherein the reflector system comprises:
a plurality of apertures; each of the plurality of apertures being operative to alter the cone angle of the light imaged on the entrance aperture of the first multiple-grating monochromator; and
means for selectively inserting one of the plurality of apertures into the path of light imaged on the entrance aperture.

34. The system of claim 32 wherein the reflector system comprises an Offner 1:1 afocal relay.

35. The system of claim 32 wherein each of the first multiple-grating monochromator and the second multiple-grating monochromator comprises a first concave optical grating and a second concave optical grating.

36. The system of claim 35 wherein the first optical grating and the second optical grating are holographic concave gratings.

37. The system of claim 35 wherein each of the first concave optical grating and the second concave optical grating is operative to pivot about a respective axis of rotation.

38. The system of claim 32 wherein the first reflection surface of the light transfer module is an excitation mirror and wherein the compound parabolic reflective surface is in reflective alignment with an emission mirror operative to output light emitted from the sample to the second multiple-grating monochromator.

39. The system of claim 38 wherein the first reflection surface of the light transfer module is a parabolic first-surface excitation mirror.

40. The system of claim 39 wherein the emission mirror is a first-surface mirror.

41. The system of claim 38 wherein the excitation mirror is positioned to direct excitation light into the opening of a selected well in a microwell plate containing as many as 5000 discrete microwells.

42. The system of claim 38 wherein the excitation light is plane polarized and wherein the light transfer module further comprises:
a first polarizing filter operative to transmit light in a plane which is parallel to the plane of the polarized excitation light;
a second polarizing filter operative to transmit light in any plane which is not parallel to the plane of the polarized excitation light; and a polarizing filter holder selectively operative to interpose one of the first polarizing filter or the second polarizing filter between the compound parabolic reflective surface and the emission mirror.

43. The system of claim 32 wherein the light transfer module, the second multiple grating monochromator, and the photodetector and analyzer are operative to analyze more than one fluorescent compound in the sample.

44. The system of claim 41 further comprising means for translating the microwell plate relative to the light transfer module allowing analysis of samples from selected ones of a plurality of wells in the microwell plate.

45. A light transfer module comprising:
an entrance aperture for admitting excitation light;
an excitation mirror operative to direct excitation light from the entrance aperture to illuminate an area such that the illuminated area emits fluorescent or luminescent light; and
a compound parabolic concentrator comprising a compound parabolic reflective surface and operative to collect and to direct light emitted from the illuminated area to an emission mirror, wherein the excitation mirror, the compound parabolic concentrator and illuminated area are substantially centered along a common axis.

46. The light transfer module of claim 45 wherein the emission mirror is operative to focus and to direct light from the compound parabolic concentrator to a monochromator as emission light.

47. The light transfer module of claim 45 wherein the emission mirror is a spherical mirror.

48. The light transfer module of claim 45 wherein the excitation mirror and the emission mirror are first-surface mirrors.

49. The light transfer module of claim 45 further comprising:
an optical filter operative to restrict the excitation light to a selected polarized plane; and
an optical filter holder selectively operative to insert the optical filter into the path of the excitation light.

50. The light transfer module of claim 49 further comprising:
a first polarizing filter operative to transmit light in a plane which is parallel to the plane of the polarized excitation light;
a second polarizing filter operative to transmit light in any plane which is not parallel to the plane of the polarized excitation light; and
a polarizing filter holder selectively operative to interpose one of the first polarizing filter or the second polarizing filter between the compound parabolic concentrator and the emission mirror.

51. A method of analyzing a sample comprising:
providing excitation light from a light source;
directing the excitation light through a first double monochromator;
transmitting the excitation light to the sample through a light transfer module;
selectively analyzing polarization of the light emitted by the sample;
employing the light transfer module to obtain light emitted by the sample;
directing the light emitted by the sample to a second double monochromator; and
analyzing light output by the second double monochromator, wherein
the light transfer module comprises first and second reflection surfaces substantially centered on a common axis with the sample, and wherein the transmitting includes redirecting the excitation light received at the first reflection surface onto the sample and wherein the directing the emitted light includes redirecting emitted light received at the second reflection surface onto the second double monochromator.

52. The method of claim 51 wherein providing excitation light comprises implementing a spherical concave reflector system.

53. The method of claim 51 wherein providing excitation light comprises implementing an Offner 1:1 afocal relay.

54. The method of claim 51 wherein the light transfer module comprises a first-surface excitation mirror positioned substantially coaxial with a sample holder supporting the sample and operative to transmit the excitation light to the sample.

55. The method of claim 51 wherein the light transfer module comprises a compound parabolic parabolic concentrator operative to obtain light emitted by the sample.

56. The method of claim 55 wherein the light transfer module further comprises a first-surface emission mirror, wherein the compound parabolic concentrator is adapted to focus light emitted by the sample to the first-surface emission mirror.

57. The method of claim 51 further comprising restricting the excitation light to a selected polarized plane.

58. The method of claim 57 the step of selectively analyzing polarization includes selectively inserting one of a plurality of polarizing filters into the light path of the light emitted by the sample.

59. The method of claim 58 wherein the selectively inserting comprises interposing one of a plurality of polarizing filters between the sample and an emission mirror operative to direct the light emitted by the sample to the second double monochromator.

60. The method of claim 51 wherein the analyzing light output by the second double monochromator comprises detecting and analyzing more than one fluorescent compound in the sample.

61. The light transfer module of claim 26 wherein the emission mirror is in off-axis alignment with the excitation mirror.

62. The light transfer module of claim 26 wherein the emission mirror is in reflective alignment with the excitation mirror.

63. The spectrophotometer system claim 32 wherein the second reflection surface is in off-axis alignment with the first reflection surface.

64. The spectrophotometer system claim 32 wherein the second reflection surface is in reflective alignment with the first reflection surface.

65. The method of claim 58 wherein the light transfer module comprises an emission mirror operative to direct light emitted by the sample to the second double monochromator, and wherein the selectively inserting comprises interposing one of a plurality of polarizing filters between the sample and the emission mirror.

* * * * *